United States Patent
Luo

(10) Patent No.: US 12,337,108 B1
(45) Date of Patent: Jun. 24, 2025

(54) NOISE-REDUCING AIR PASSAGE DEVICE AND ITS COMPONENTS FOR USE IN VENTILATOR SYSTEMS

(71) Applicant: WALLENBERG UNION LLC, Newark, DE (US)

(72) Inventor: David Luo, Newark, DE (US)

(73) Assignee: WALLENBERG UNION LLC, Newark, DE (US)

( * ) Notice: Subject to any disclaimer, the term of this patent is extended or adjusted under 35 U.S.C. 154(b) by 0 days.

(21) Appl. No.: 18/784,481

(22) Filed: Jul. 25, 2024

(51) Int. Cl.
*A61M 16/00* (2006.01)

(52) U.S. Cl.
CPC .... *A61M 16/0066* (2013.01); *A61M 16/0003* (2014.02); *A61M 2202/0007* (2013.01); *A61M 2202/02* (2013.01); *A61M 2205/0216* (2013.01); *A61M 2205/025* (2013.01); *A61M 2205/103* (2013.01); *A61M 2205/3331* (2013.01); *A61M 2205/42* (2013.01)

(58) Field of Classification Search
CPC .......... A61M 16/0066; A61M 16/0003; A61M 2205/42
See application file for complete search history.

(56) References Cited

U.S. PATENT DOCUMENTS

| | | | | |
|---|---|---|---|---|
| 5,397,950 A * | 3/1995 | Norbury, Jr. | ........... | H02K 1/187 310/58 |
| 2005/0103339 A1 | 5/2005 | Daly et al. | | |
| 2007/0277827 A1 | 12/2007 | Bordewick et al. | | |
| 2008/0304986 A1 * | 12/2008 | Kenyon | ................. | H02K 5/225 417/423.12 |
| 2009/0007912 A1 | 1/2009 | Lindell et al. | | |
| 2010/0307498 A1 | 12/2010 | Jones et al. | | |
| 2012/0167879 A1 | 7/2012 | Bowman et al. | | |
| 2013/0263854 A1 | 10/2013 | Taylor et al. | | |
| 2014/0158131 A1 * | 6/2014 | Kenyon | ............ | A61M 16/0066 128/204.18 |
| 2014/0299130 A1 | 10/2014 | Librett et al. | | |
| 2014/0299132 A1 * | 10/2014 | Librett | .............. | A61M 16/0066 128/205.25 |
| 2015/0059745 A1 | 3/2015 | Barker et al. | | |

(Continued)

FOREIGN PATENT DOCUMENTS

| CN | 104132003 | 11/2014 |
|---|---|---|
| CN | 117145810 | 12/2023 |

(Continued)

*Primary Examiner* — Margaret M Luarca
(74) *Attorney, Agent, or Firm* — HSML P.C.

(57) ABSTRACT

A noise-reducing air passage device and its components for use in ventilator systems, including a housing with at least one inlet, at least one outlet, an inner wall, and an outer wall. The space enclosed by the inner wall of the housing forms a gas passage including at least one chamber to provide a space for gas accumulation and flow. A blower, the core component to provide positive pressure gas to the device, is secured within one of the at least one chamber. The gas passage also includes a ventilation component to divide the gas and streamline turbulent airflow. The ventilation component is among the noise-reducing components, which also include a support component to provide support and damp vibrations for the blower and an inlet component provided at the inlet.

25 Claims, 28 Drawing Sheets

(56) References Cited

U.S. PATENT DOCUMENTS

| | | | |
|---|---|---|---|
| 2015/0320960 A1* | 11/2015 | Barlow | A61M 16/021 128/205.25 |
| 2020/0188616 A1 | 6/2020 | Kenyon et al. | |
| 2023/0398318 A1 | 12/2023 | Mazzone | |
| 2024/0207545 A1 | 6/2024 | Chen et al. | |

FOREIGN PATENT DOCUMENTS

| | | |
|---|---|---|
| CN | 117553038 | 2/2024 |
| WO | 2024017377 | 1/2024 |

* cited by examiner

NOISE-REDUCING AIR PASSAGE DEVICE AND ITS COMPONENTS FOR USE IN VENTILATOR SYSTEMS

TECHNICAL FIELD

This disclosure pertains to a noise-reducing air passage device and its components for use in ventilator systems. The noise-reducing air passage device and its components include at least one chamber, a blower, a ventilation component, and a support component.

BACKGROUND

Snoring occurs during sleep due to a reduction in muscle tone in the patient's airway, causing the airways to be compressed and air flow to be obstructed. This results in vibrations of the soft palate and the base of the tongue, leading to the production of sound or even episodes of apnea. Statistics show that more than half of adults worldwide have experienced varying degrees of snoring. If persistent, snoring may lead to risks such as sleep apnea or even cessation of breathing, and severe complications can arise, potentially threatening life. Therefore, respiratory-related diseases should be treated promptly to prevent the development of serious consequences. Here are seven common causes of sleep disorders: 1. Aging: As one reaches middle age, the muscle tone in the throat gradually weakens or relaxes, increasing the airflow and mucosal friction in the airway, leading to snoring. 2. Obesity: In obese individuals, insufficient muscle tone in the airway can lead to collapse, and fat accumulation around the airways thickens the muscles and narrows the airways, making it difficult for the patient to breathe smoothly during sleep. 3. Long-term smoking or drinking before bed: Both smoking and drinking can damage the airway smooth muscles and mucosa, dull the autonomic nervous system's response, and cause respiratory muscles to relax, leading to snoring during sleep. 4. Small or retracted lower jaw: A small or retracted lower jaw can compress the airway, preventing normal air entry and resulting in snoring. 5. Taking sedatives or sleeping pills: These can reduce the muscle tone of the airway, causing relaxation and blockage, leading to snoring or breathing difficulties. 6. Nasal disorders: Conditions like chronic rhinitis, deviated nasal septum, or nasal polyps can lead to nasal congestion or relaxation and sagging of the soft palate muscles near the throat, increasing the likelihood of snoring. 7. Enlarged tonsils: If the airway is occupied and compressed by enlarged tonsils, it can narrow and cause the patient to snore. Although snoring is a common issue, some patients experience more severe effects than others, impacting their sleep quality. Sleep-related breathing disorders are an independent risk factor for hypertension, and severe sleep-disordered breathing often accompanies sleep apnea syndrome. For doctors, the main assessment goal is to identify populations at high risk for obstructive sleep apnea (OSA). This includes inspecting the nose and mouth for signs of airway obstruction and risk factors for snoring-such as nasal polyps, a deviated nasal septum, chronic nasal congestion, a high arched palate, a jaw that is small or farther back than normal, and an enlarged tongue, tonsils, or uvula (the structure that hangs down at the back of the throat). Patients in these groups are prone to diseases related to OSA, particularly hypertension, heart disease, stroke, acid reflux, atrial fibrillation (arrhythmia), depression, and diabetes. Not all snorers have OSA, but most patients with OSA snore, hence snoring should not be ignored in daily life. Preventing snoring and the potential for OSA is crucial for maintaining overall health.

This disclosure relates to the prevention and treatment of sleep-disordered breathing. It aims to provide a stable airflow to the airway to keep the patient's airway open, effectively reducing symptoms of snoring and OSA. This treatment method, which involves providing continuous airflow through a Continuous Positive Airway Pressure (CPAP) machine to prevent airway collapse during breathing while asleep, not only improves sleep-disordered breathing issues but also reduces health risks associated with OSA. It improves the patient's sleep quality and can decrease the risk of respiratory-related cardiovascular diseases and daytime fatigue. Recognizing and adopting effective pressure therapy is imperative and necessary to improve sleep-disordered breathing issues and enhance overall quality of life.

SUMMARY

The objective of this disclosure is to provide a novel noise-reducing air passage device and its components for use in ventilator systems, which not only achieve noise reduction but also ensure patient health and safety. This design is easier to manufacture and can quickly adapt to market needs. The internally foam-reduced noise-reducing air passage device can be used by patients over extended periods, overcoming limitations of similar existing technologies. It provides a more effective solution with broader application scenarios and safer treatment methods, supplying continuous positive air pressure to treat sleep-related breathing disorders.

In one embodiment, a noise-reducing air passage device and its components for use in ventilator systems are provided, configured to provide pressurized gas to an airway of a patient. The noise-reducing air passage device and its components at least include a housing, a blower, an inlet component, a ventilation component and a support component. The housing includes at least one inlet, at least one outlet, an inner wall, and an outer wall. The space enclosed by the inner wall of the housing forms a gas passage including at least one chamber to provide a space for gas accumulation and flow. The blower is secured within the chamber to pressurize gas and deliver the pressurized gas to the outlet. The inlet component has a wall. The inlet component is configured to guide the gas gently into the at least one chamber and at least one portion of the wall extends outwardly. At least one ventilation component is provided within the gas passage and configured to divide at least part of the gas. The support component is configured as a perforated elastomer and at least one support component is provided within the chamber to support the blower and to disperse vibrations during operation of the blower.

In one embodiment, the ventilation component has an exhaust end that allows gas to flow out, with a distance between the exhaust end and its opposing inner wall of the housing being at least 1.5 times a width of the ventilation component In one embodiment, the at least one portion of the wall that extends outwardly forms an angle between 0.5° to 75° with the wall of the inlet component.

In one embodiment, a length of the at least one portion of the wall that extends outwardly is between 3 mm to 10 mm.

In one embodiment, the support component has at least two different thicknesses.

In one embodiment, the housing of the noise-reducing air passage device forms part of the positive pressure ventilation device.

In one embodiment, the housing of the noise-reducing air passage device includes one of the following materials: polypropylene, polycarbonate, polyethylene terephthalate-1, 4-cyclohexane dimethanol ester, polyamide, or polyetheretherketone.

In another embodiment, a noise-reducing air passage device and its components for use in ventilator systems are provided, configured to provide pressurized gas to an airway of a patient. The noise-reducing air passage device and its components at least include a housing, a blower and a ventilation component. The housing includes at least one inlet, at least one outlet, an inner wall, and an outer wall. The space enclosed by the inner wall of the housing forms a gas passage including at least one chamber to provide a space for gas accumulation and flow. The blower is secured within the chamber, configured to pressurize gas and deliver the pressurized gas to the outlet. And at least one ventilation component is provided within the gas passage and configured to divide at least part of the gas. A distance from an intake end to an exhaust end of the ventilation component is greater than 10 mm, and a distance from the exhaust end of the ventilation component to its opposing inner wall of the housing is greater than or equal to 5 mm.

In one embodiment, the ventilation component is secured within the housing and has internal gaps, configured to divide the gas flowing out from the chamber.

In one embodiment, the internal gaps of the ventilation component have a width between 0.5 mm to 3.3 mm.

In one embodiment, an inlet component is provided at the inlet, and a hardness of the inlet component is between Shore A20 to Shore A80.

In one embodiment, the blower has an inlet port, and a straight-line distance between the exhaust end of the ventilation component and the inlet port of the blower is less than or equal to 15 mm.

In one embodiment, the ventilation component includes one of the following materials: polypropylene, polycarbonate, polyethylene terephthalate-1,4-cyclohexane dimethanol ester, polyamide, or polyetheretherketone.

In yet another embodiment, a noise-reducing air passage device and its components for use in ventilator systems are provided, configured to provide pressurized gas to an airway of a patient. The noise-reducing air passage device and its components at least include a housing, a blower and a support component. The housing includes at least one inlet, at least one outlet, an inner wall, and an outer wall. The space enclosed by the inner wall of the housing forms a gas passage including at least one chamber to provide a space for gas accumulation and flow. The blower is secured within the chamber, configured to pressurize gas and deliver the pressurized gas to the outlet. And the support component is configured as a perforated elastomer and at least one support component is provided within the chamber to support the blower and to disperse vibrations during operation of the blower. And the support component has at least one of the following characteristics: a) at least part of the support component in contact with the inner wall of the housing; b) at least part of the wall thickness of the support component within a range between 0.6 mm to 3 mm; and c) a hardness of the support component between Shore A20 to Shore A80.

In one embodiment, the at least one chamber further includes a first chamber and a second chamber, and the blower is provided within the first chamber.

In one embodiment, at least part of the support component has a non-uniform wall thickness.

In one embodiment, a contact area between the support component and the blower is at least 330 mm$^2$.

In one embodiment, an outlet pipe is provided at the at least one outlet and is configured to be integrally formed with the housing.

In one embodiment, the support component includes one of the following materials: silicone, rubber, thermoplastic elastomer, thermoplastic polyurethane, or fluororubber.

In another embodiment, a noise-reducing air passage device and its components for use in ventilator systems are provided, configured to provide pressurized gas to an airway of a patient. The noise-reducing air passage device and its components at least include a housing, a blower, a ventilation component and a support component. The housing includes at least one inlet, at least one outlet, an inner wall, and an outer wall. The space enclosed by the inner wall of the housing forms a gas passage including at least one chamber to provide a space for gas accumulation and flow. The blower is secured within the chamber, configured to pressurize gas and deliver the pressurized gas to the outlet. At least one ventilation component is provided within the gas passage and configured to divide at least part of the gas. A distance from an intake end to an exhaust end of the ventilation component is greater than 10 mm, and a distance between the exhaust end of the ventilation component and its opposing inner wall of the housing is greater than or equal to 5 mm. The support component is configured as a perforated elastomer and at least one support component is provided within the chamber to support the blower and to disperse vibrations during operation of the blower. A thickness of at least part of the support component wall is between 0.6 mm to 3 mm.

In one embodiment, the at least one chamber further includes a first chamber and a second chamber.

In one embodiment, the at least one ventilation component communicates with the first chamber and the second chamber, and parts of the at least one ventilation component are present in both chambers.

In one embodiment, the ventilation component is secured within the housing and has internal gaps, configured to divide the gas flowing out from the first chamber.

In one embodiment, multiple ventilation components, configured to fit against each other, are provided within the gas passage, with their internal gaps interconnectable.

In one embodiment, the support component includes one of the following materials: silicone, rubber, thermoplastic polyurethane, thermoplastic elastomer, or fluoroelastomer.

The implementation of a noise-reducing air passage device and its components at least includes the following benefits:

1. The disclosure utilizes various efficient noise-reducing components (such as inlet components, ventilation components, and support components) and structures within the noise-reducing air passage device. These include optimizing the volume ratio of the gas passage to the blower and designing the structure to extend the airflow path inside the air passage device. The combination of these noise-reducing components and structures, along with the layered arrangement of various noise-reducing components, effectively reduces noise by at least 15 decibels, thus meeting noise level requirements in FDA regulations. Most ventilators currently available on the market utilize foam as the primary noise-reducing material within their air passage devices. This not only poses potential health risks to patients, but also suffers from a decrease in noise reduction effectiveness over time due to foam degradation. In contrast to these traditional designs, which depend almost entirely on foam for noise reduction, this disclosure innovates by using the structure of the air passage device itself as the primary noise reduction method. This achieves regulatory noise levels with less or no foam usage. The noise-reducing structures and components in this disclosure use innovative designs and advanced materials to minimize noise transmission in the airflow, ensuring optimal silence during ventilator operation. Reducing noise through structure and components also decreases the potential for reduced airflow and volume, further enhancing the stability of ventilator performance. Overall, this efficient noise-reduction design not only improves patient comfort but also effectively reduces environmental noise, providing a quiet and comfortable sleep environment for the patient.

2. The design of efficient noise-reducing ventilation components offers advantages over traditional noise-reducing elements in terms of cost, installation, structure, and applicability. 1) This disclosure innovatively designs and uses ventilation components that achieve good noise reduction. Specifically, it smooths the originally chaotic airflow by channeling it through specific internal gaps within the structure. This process reduces noise by preventing the formation of turbulent flows or divergent air paths. As a single basic structural unit itself, this ventilation component has a straightforward design and is capable of reducing noise by at least 2 decibels, making it a notably efficient solution for noise reduction in its application. 2) The compact size of the ventilation component provided by this disclosure allows for a rational layout within the ventilator, occupying less space. Multiple ventilation components can be combined within the air passage device for enhanced noise reduction. Due to their simple structure, these ventilation components can be modified according to the space in the noise-reducing air passage device to become a standard structural formula, adaptable to different types of air passage devices, such as the ventilation component having a circular shape to match a circular channel in a noise-reducing air passage device. 3) Furthermore, the ventilation component is made from a single material and has a simple structure, simplifying the manufacturing process and making costs more controllable. The uniformity in structure and material allows manufacturers to scale production more easily and reduce costs through material optimization and process improvements. In contrast, existing ventilators in the market involve noise-reducing devices made from various materials with complex structures, making their manufacturing more cumbersome and costly. Therefore, the ventilation component provided by this disclosure offer a cost-effective advantage, providing patients with high-value products and promoting technical innovation and cost reduction in the ventilator industry.

3. The noise-reducing components used in the disclosure are detachable and can be used independently. While retaining the structure, their shape can be customized to fit various forms of noise-reducing air passage devices. Not only does the disclosure incorporate smooth and longer airflow paths to achieve noise reduction, but it also features several different types of detachable noise-reducing components that can be used independently. 1) These detachable noise-reducing components, such as inlet components, ventilation components, and support components, can be customized in shape and size to fit different forms and specifications of noise-reducing air passage devices. This provides a universal noise reduction solution for various models of ventilators, enhancing the product's applicability. In one approach, these detachable parts can be standardized to serve as universal components suitable for different noise-reducing air passage devices. In this way, manufacturers can produce large quantities of universal parts, thereby reducing production costs and enhancing production efficiency. 2) Since these noise-reducing components are used independently and are detachable, they can be replaced, maintained, and upgraded separately from the noise-reducing air passage devices. This reduces the ventilator's overall maintenance costs and future iteration costs. Furthermore, this form allows easy replacement or upgrading of noise-reducing components based on patient needs, meeting different requirements for noise reduction or personal preferences. This flexibility and customizability of the noise-reducing components provide a better experience for patients and bring more convenience in the use and maintenance of ventilators.

4. The noise-reducing components and structures provided by the disclosure can achieve regulatory noise levels within the air passage devices without using foam. Compared to existing ventilators on the market that almost always include foam in their noise-reducing air passage devices, this design enhances device safety, service life, and is environmentally friendly. The noise-reducing components and structures in this disclosure incorporate a series of innovative designs supported by theoretical and experimental data, resulting in a noise-reducing air passage device that lowers noise levels and still meets the regulatory requirements for noise levels without the use of foam. The benefits of reducing foam in the noise-reducing air passage devices can at least include: 1) Since placing foam within air passage devices is a common and effective method to meet regulatory noise levels, almost all respiratory machines on the market currently use foam materials in the air passage devices. However, tiny particles from decomposed foam materials can pose health risks when inhaled, particularly in respiratory machines used for prolonged periods and for long durations each time. Foam impacts human health in several significant ways: a. Chemical Exposure: Foam is typically made from synthetic materials such as polyurethane and polyether, which often include chemical additives or components. These chemicals can be released into the air during the ventilator's operation, becoming airborne contaminants. Prolonged inhalation of these substances can negatively affect both the respiratory system and overall health. b. Microbial Growth: Foam has moisture-absorbing properties, and in the humid environment created by ventilators, this can lead to the growth of bacteria and mold. Some ventilators also have humidification systems to increase patient comfort, which further enhances moisture absorption by the foam and promotes microbial growth. c. Particle Release: When the noise-reducing air passage device is in operation, the airflow causes the foam to vibrate and rub against other surfaces, leading to material degradation. This degradation can produce small particles. Additionally, the microbial growth in the foam due to its moisture retention can also lead to decomposition of the foam, releasing more particles. These particles are then inhaled by the patient, posing serious health risks. Furthermore, some patients may experience allergic reactions to foam, which can trigger respiratory allergies or asthma attacks, adversely affecting respiratory health. The noise-reducing air passage device in this disclosure achieves the regulatory noise levels with reduced use of foam or without foam, thereby reducing these health hazards. This not only ensures a safer respiratory environment for patients but also increases the competitiveness in the market, as it provides a health-conscious alternative to traditional designs. 2) Foam materials age and deteriorate quickly, making them the shortest-lived material within noise-reducing air passage devices compared to plastic materials. The presence of foam in existing designs reduces the lifespan of these air passage devices. This disclosure allows patients to opt for air passage devices with reduced foam, thereby extending the overall lifespan of the ventilator. Moreover, the absence of foam simplifies the internal structure of the noise-reducing air passage device. It eliminates the need for additional foam-fixing structures, reducing mechanical wear and maintenance needs, and enhancing the device's reliability and stability. 3) Foam, while a common noise-reduction material in ventilators, effectively reduces noise but has environmental impacts during its manufacture, use, and disposal. As a synthetic material, foam production consumes significant energy and resources and may involve the use of chemicals that contribute to pollution. Additionally, high-quality noise-reducing foam materials are usually costly, which, while reducing health risks, also increases the purchase cost of the device. The design of air passage devices with reduced foam reduces these issues. It not only lessens the negative environmental impact but also reduces waste production and saves costs on foam material purchases. 4) Reduced-foam air passage devices that still meet regulatory noise levels provide patients with more flexible options. Patients can choose whether to have foam within the noise-reducing air passage device or not. For those requiring quieter environments, such as patients with high demands for silence to improve sleep quality, they can opt for the noise-reducing device provided in this disclosure in combination with foam. Additionally, incorporating health-friendly materials like silicone or rubber within the noise-reducing air passage device can also reduce noise to some extent while eliminating the negative effects of foam.

DETAILED DESCRIPTION

Figure 1:
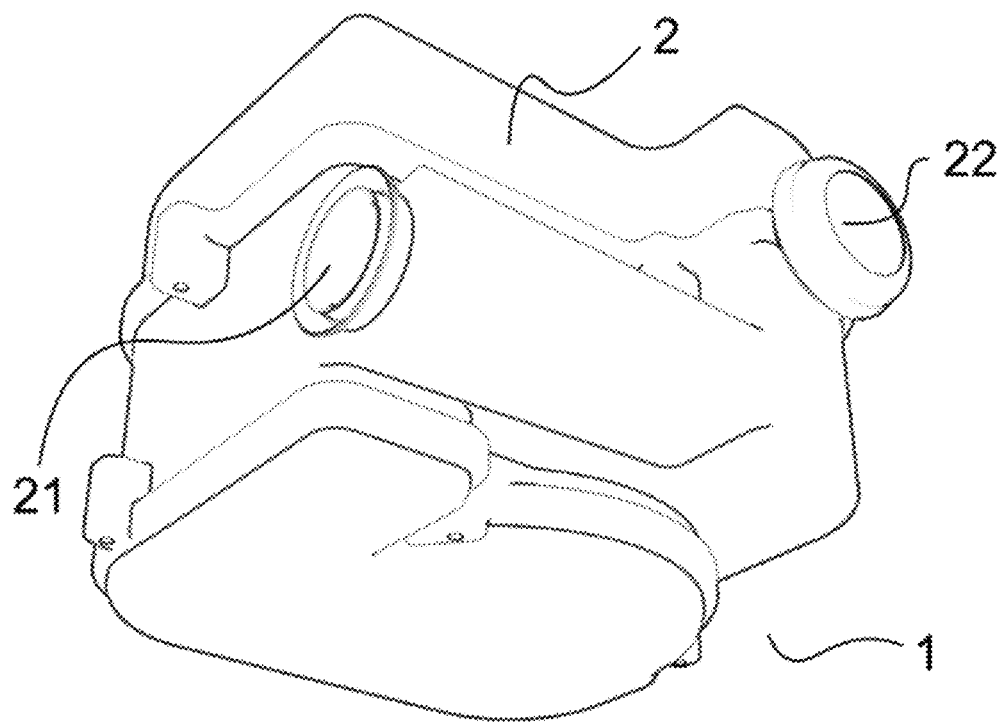
FIG. 1 is a three-dimensional schematic diagram of the housing of the noise-reducing air passage device and its components in accordance with one embodiment.
Figure 2:
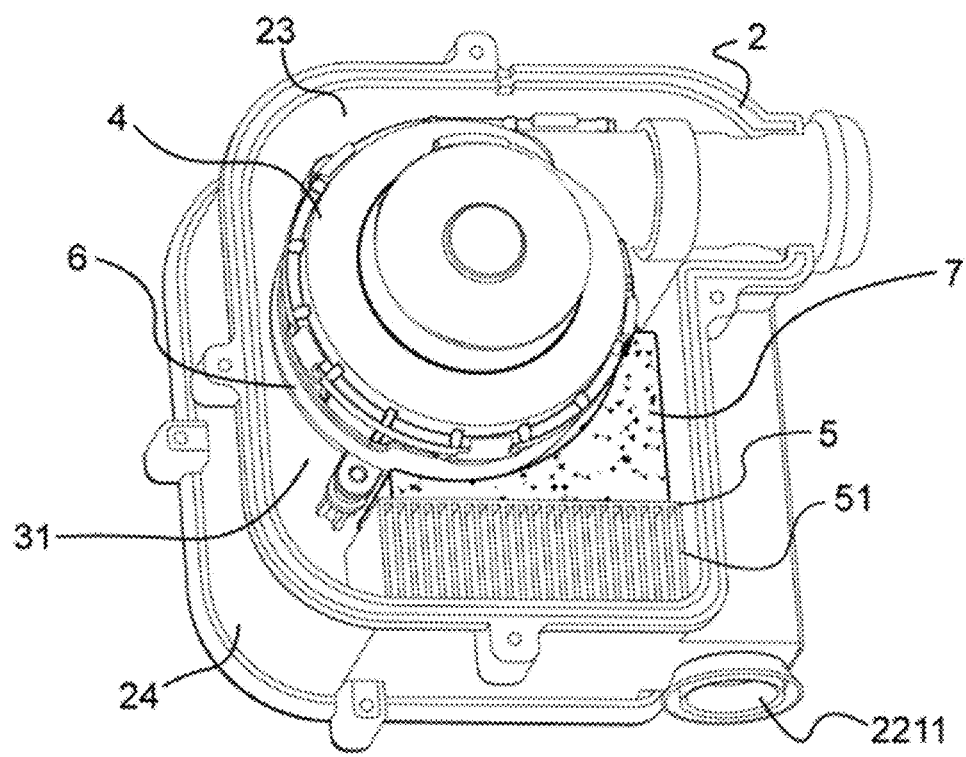
FIG. 2 is a three-dimensional schematic diagram of the internal structure of the noise-reducing air passage device and its components in accordance with one embodiment.
Figure 3:
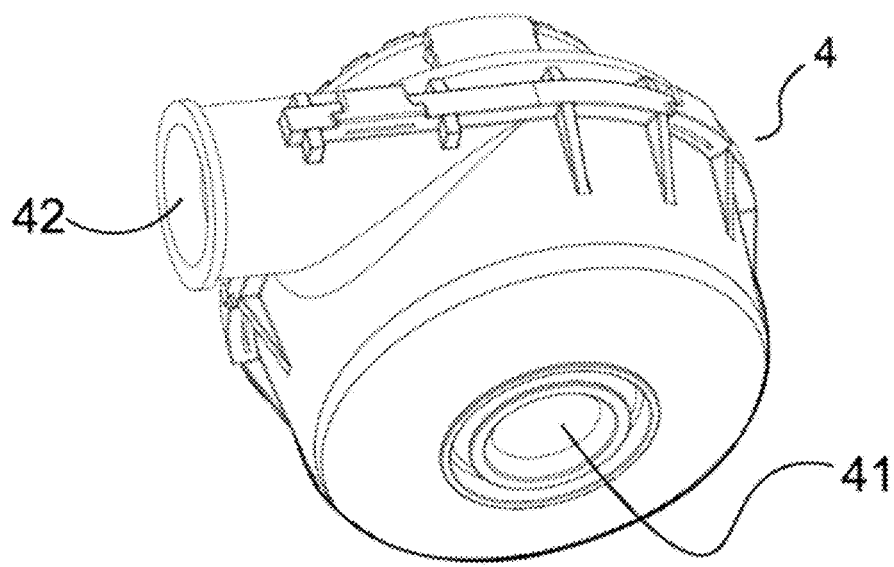
FIG. 3 is a three-dimensional schematic diagram of the blower of the noise-reducing air passage device and its components in accordance with one embodiment.
Figure 4:
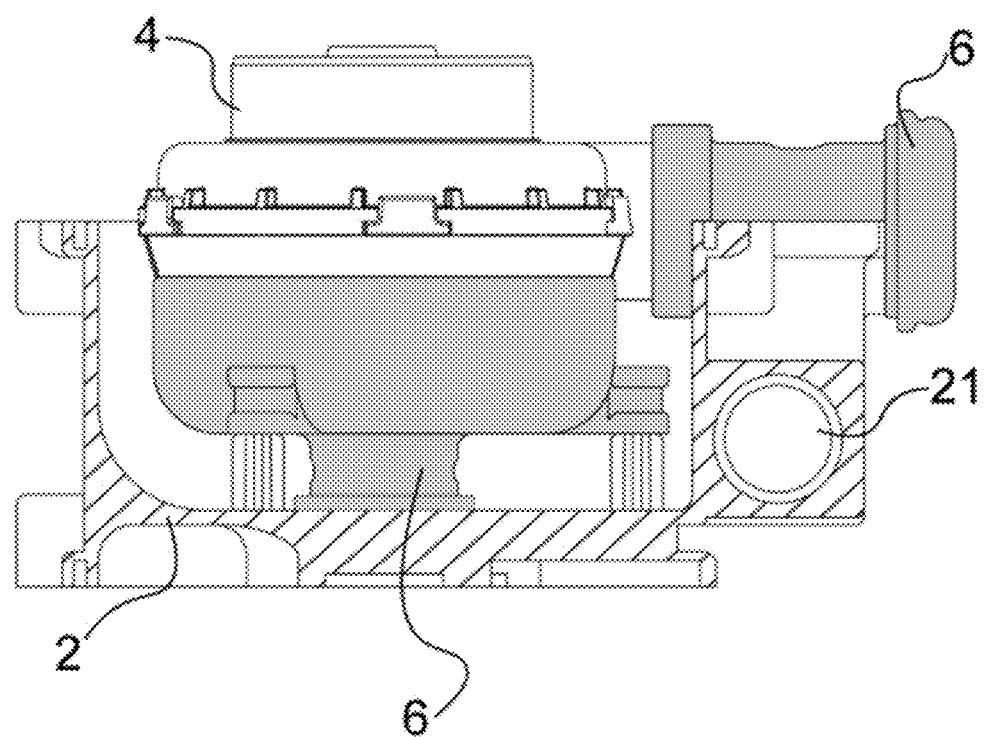
FIG. 4 is a three-dimensional schematic diagram of the support component of the noise-reducing air passage device and its components in accordance with one embodiment.
Figure 5:
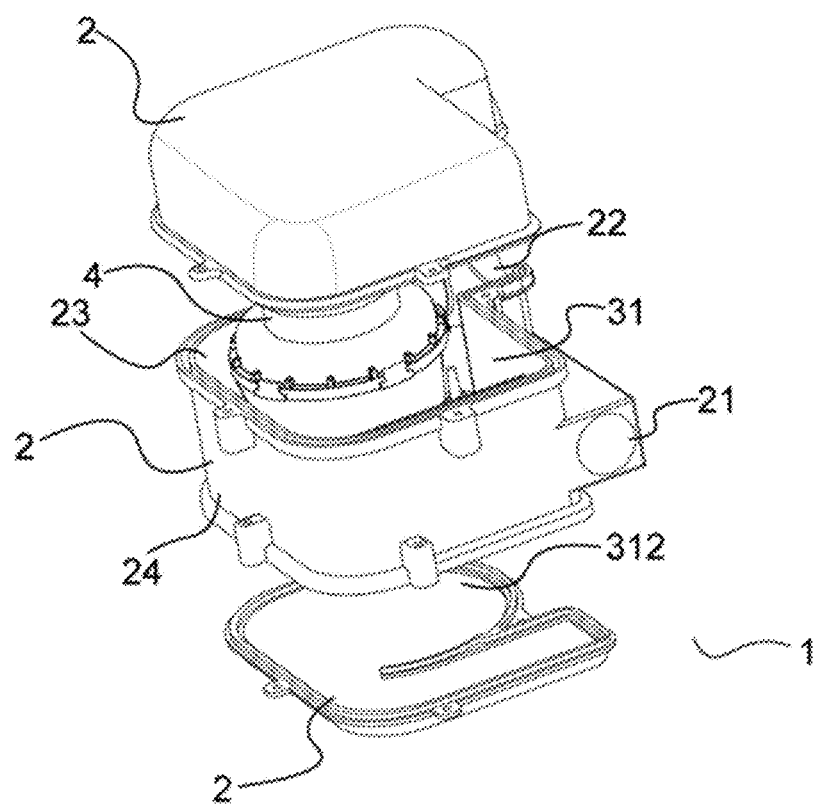
FIG. 5 is an exploded view of the housing of the noise-reducing air passage device and its components in accordance with one embodiment.
Figure 6:
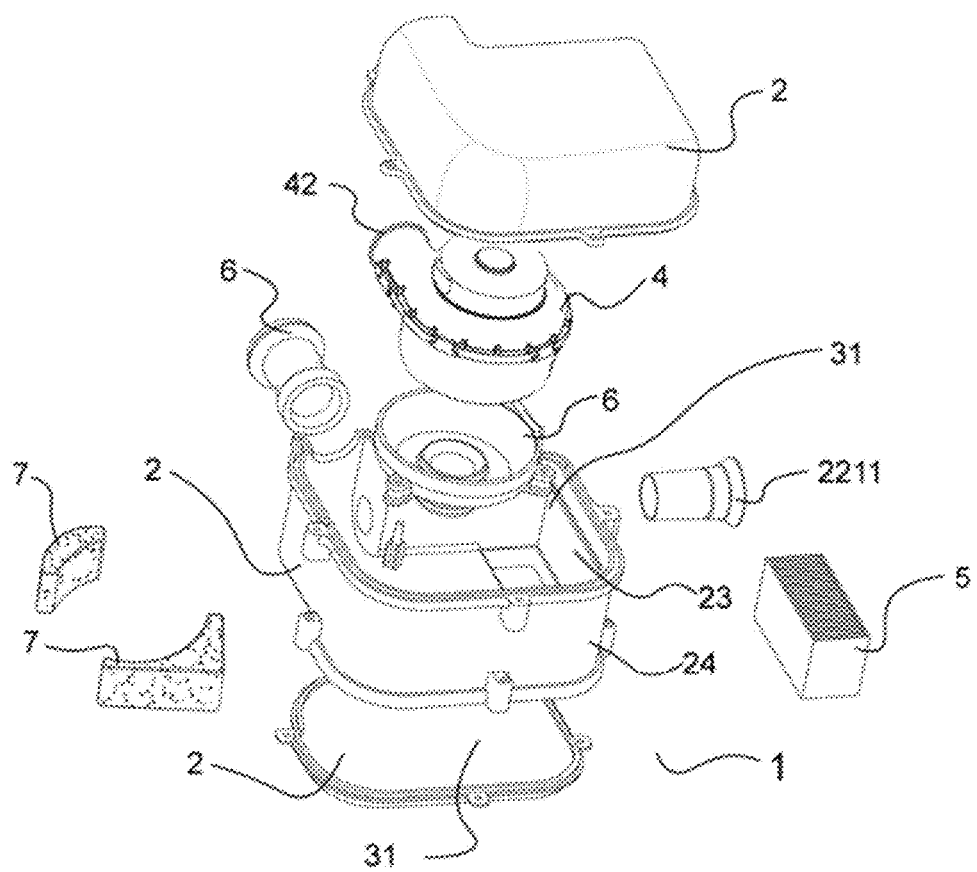
FIG. 6 is an exploded structure view of the noise-reducing air passage device and its components in accordance with one embodiment.
Figure 7:
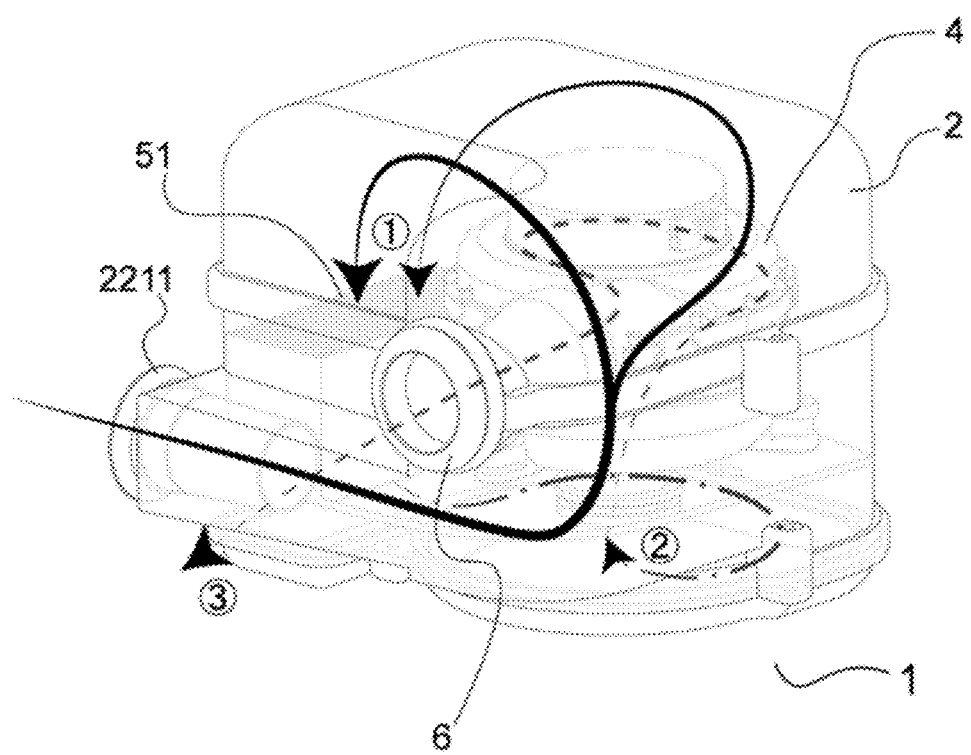
FIG. 7 is an airflow path diagram of the noise-reducing air passage device and its components in accordance with one embodiment.
Figure 8:
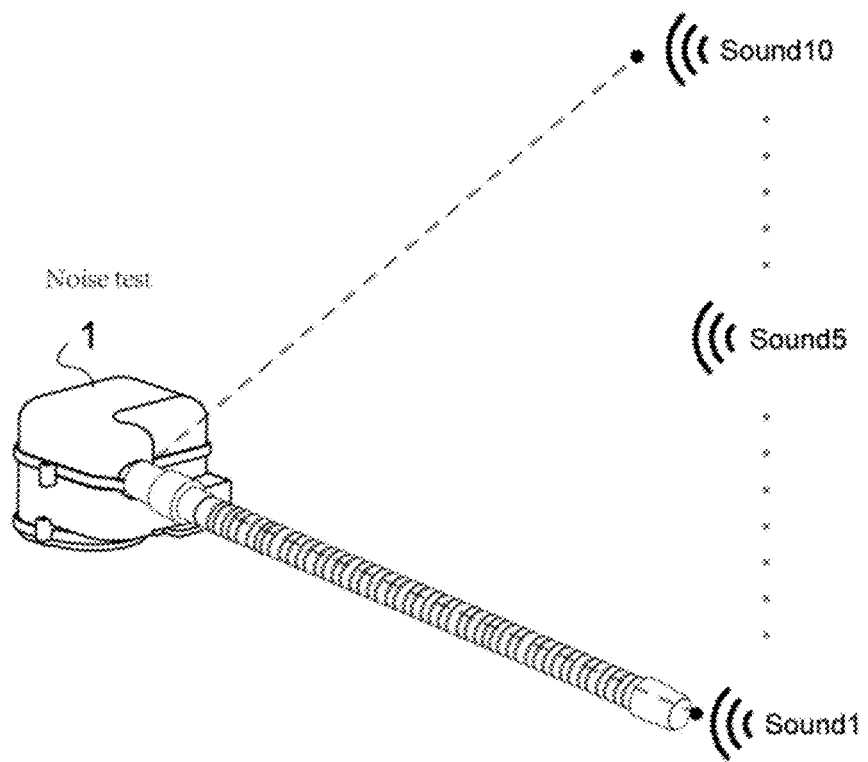
FIG. 8 is a test schematic diagram of the noise-reducing air passage device and its components in accordance with one embodiment.
Figure 9:
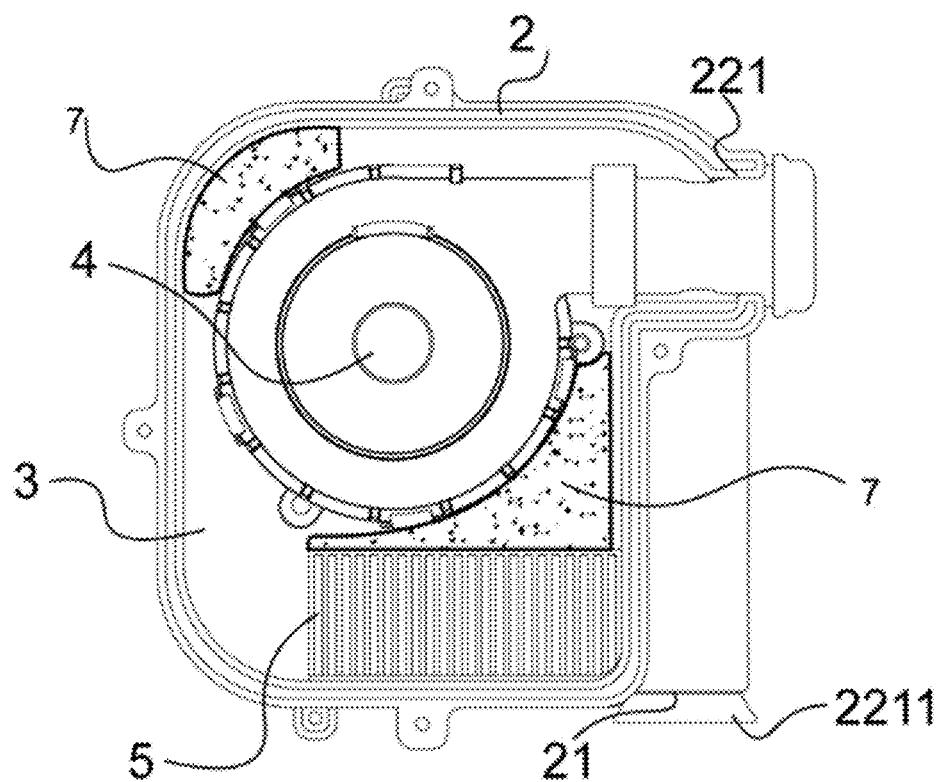
FIG. 9 is a top view of the internal structure of the noise-reducing air passage device and its components in accordance with one embodiment.
Figure 10:
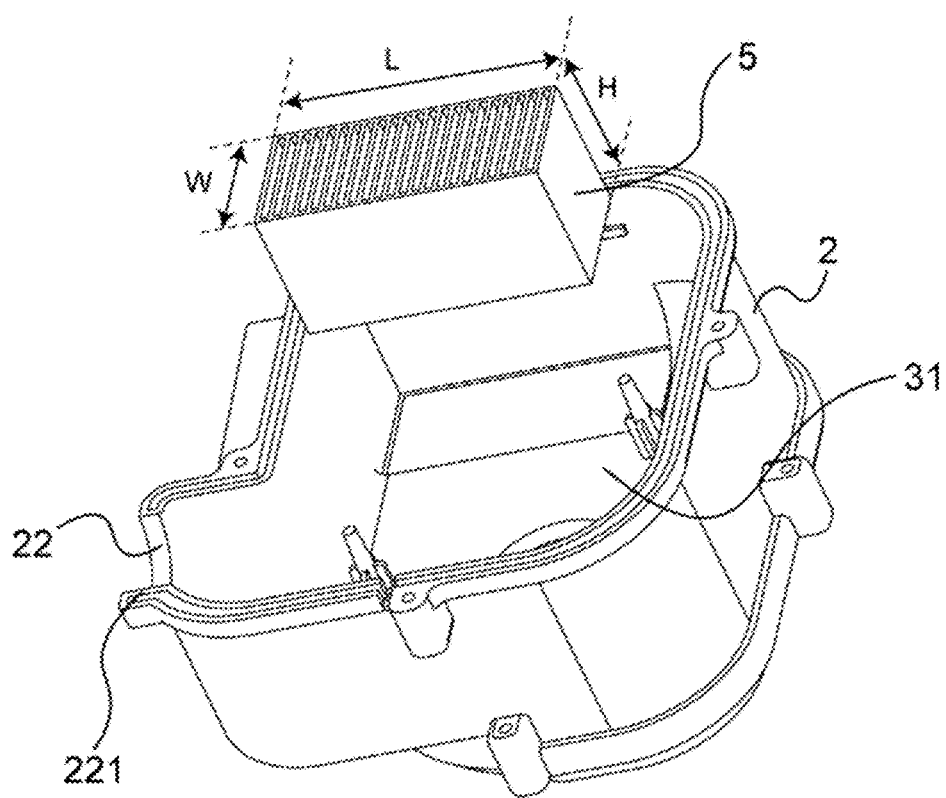
FIG. 10 is a schematic diagram of the ventilation component of the noise-reducing air passage device and its components in accordance with one embodiment.
Figure 11:
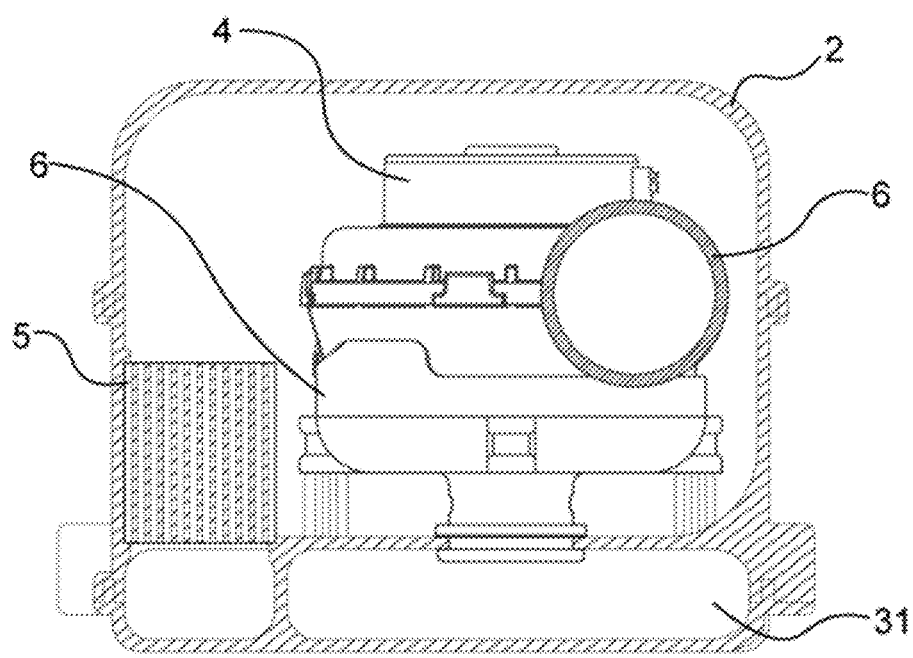
FIG. 11 is a cross-sectional view of the ventilation component of the noise-reducing air passage device and its components in accordance with one embodiment.

To facilitate the understanding of the disclosure, a more comprehensive description will be provided with reference to the relevant drawings. The drawings illustrate typical embodiments of the disclosure. However, the disclosure can be implemented in many different forms and is not limited to the embodiments described herein. On the contrary, the embodiments are provided to make the disclosure more thorough and comprehensive.

Unless otherwise defined, all technical and scientific terms used herein have the same meaning as commonly understood by one of ordinary skill in the art to which this disclosure belongs. The terms used in the specification of the disclosure herein are for the purpose of describing particular embodiments only rather than limiting the disclosure.

The present disclosure addresses the issues associated with existing noise-reducing air passage devices in ventilator systems that rely on foam for noise reduction. These issues include foam degradation, potential health risks to patients, complex manufacturing processes, and environmental concerns. This disclosure offers a safer, more reliable, and structurally simpler noise-reducing air passage device and its components, which optimizes the existing configurations by incorporating noise-reducing components within the air passage device, achieving the regulatory noise level without relying heavily on foam. This disclosure benefits patients, manufacturers, and the market by providing an advanced technical solution that is also environmentally sustainable.

Detailed embodiments are presented below to elucidate the configurations of the noise-reducing air passage device 1 for use in ventilator systems.

Embodiment 1

This embodiment provides a noise-reducing air passage device 1 and its components for use in ventilator systems. It includes three-dimensional schematic diagrams, exploded views, an airflow path diagram, a test schematic diagram, a top view, cross-sectional views, and various data illustrations (refer to FIGS. 1-15). This embodiment pertains to a device used to treat respiratory conditions such as obstructive sleep apnea, that is, the noise-reducing air passage device 1 and its components. The noise-reducing air passage device 1 and its components include a housing 2 with at least one inlet 21, at least one outlet 22, an inner wall 23, and an outer wall 24. The space enclosed by the inner wall 23 of the housing 2 forms a gas passage 3 including at least one chamber 31, to provide a space for gas accumulation and flow. A blower 4 is situated within the chamber 31 to provide pressurized gas for the noise-reducing air passage device 1. The device 1 also includes a ventilation component 5, a support component 6 for the blower 4, and an inlet component 2211, all working together to reduce noise as air flows in and out of the blower 4, ensuring the device 1 meets regulatory noise levels and provides a comfortable experience for patients.

Specifically, the housing 2 of the noise-reducing air passage device 1 and its components has at least one inlet 21, at least one outlet 22, an inner wall 23, and an outer wall 24. The inlet 21 is configured to draw air from the external environment into the chamber 31 for pressurization. The inlet 21 can take many forms. In this embodiment, the inlet 21 is a cylindrical passage, either integrally formed with or separate from the housing 2, guiding air into the chamber 31. The passage can also be non-cylindrical shapes like square or oval, or any other shapes suitable for ventilation. The inlet 21 serves as the entry point for air into the housing 2. The outlet 22 on the housing 2 is configured to communicate with the blower outlet port 42. This communication implies that outlet 22 can directly connect to the blower outlet port 42 for ventilation, or it can be linked through one or more external components to facilitate airflow between the outlet 22 and the blower outlet port 42. The external components include an outlet pipe 221 connectable to the outlet 22, which may be either integrally formed with or separate from the housing 2. In some instances, an outlet pipe 221 is integrally formed with the housing 2 at the outlet 22. Due to typically higher noise levels at the inlet 21 compared to the outlet 22, placing them on different walls can prevent noise accumulation. During operation, the space enclosed by the inner wall 23 forms the gas passage 3, designed with specific volume requirements to enhance noise reduction. Multiple tests comparing various gas passage 3 to blower 4 volume ratios in the noise-reducing air passage device 1 show that the gas passage 3 should have a volume at least three times greater than that of the blower 4 for a better noise reduction effect. Preferably, a volume ratio between 3 and 16 times larger results in optimal noise reduction for the gas passage 3. The space enclosed by the inner wall 23 of the housing 2 forms a gas passage 3 including at least one chamber 31, to provide a space for gas accumulation and flow. During ventilator operation, the airflow path starts at the inlet 21, flows into the chamber 31, and reaches the inlet port 41 of the blower 4 via the designated path within the noise-reducing air passage device 1. The air is pressurized inside the blower 4 and then exits through the outlet 22. The airflow path can be either a basic horizontal form, where the airflow largely remains on the same horizontal plane, or it can take the form of a spatial gas passage with significant vertical routes (having a vertical path of at least 20 mm). In some implementations, the inner wall 23 forms at least two chambers 31 within the gas passage 3, usually adjacent to each other. For example, the inner wall 23 forms a first chamber and a second chamber within the gas passage 3, with the blower 4 provided within the first chamber. The blower 4 is secured within the first chamber and configured to pressurize and direct air to the outlet 22. Additionally, the housing 2 of the noise-reducing air passage device 1 is made from one of the following materials: polypropylene, polycarbonate, polyethylene terephthalate-1,4-cyclohexane dimethanol ester, polyamide, or polyetheretherketone.

Figure 12:
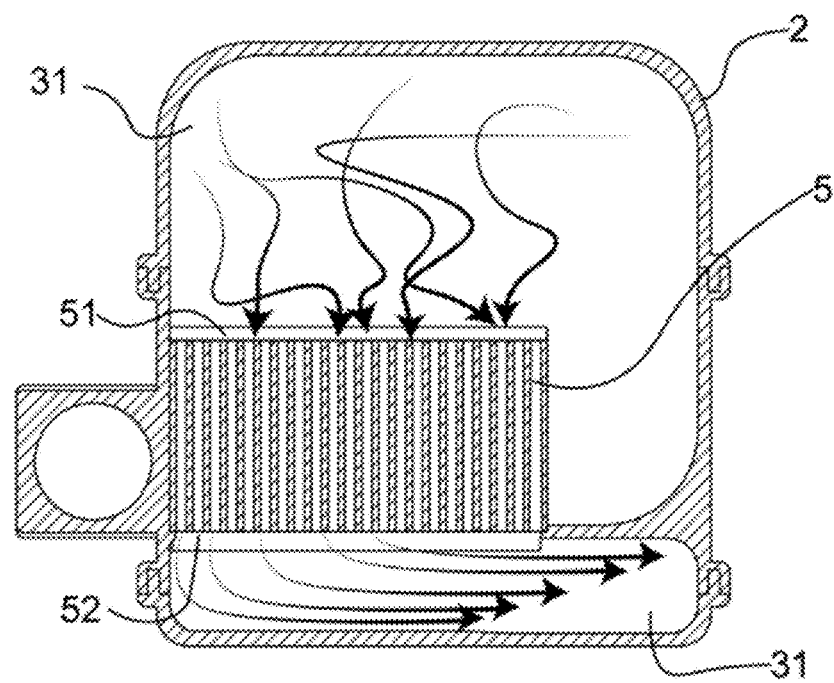
FIG. 12 is a schematic diagram of the airflow passing through the ventilation component of the noise-reducing air passage device and its components in accordance with one embodiment.
Figure 13:
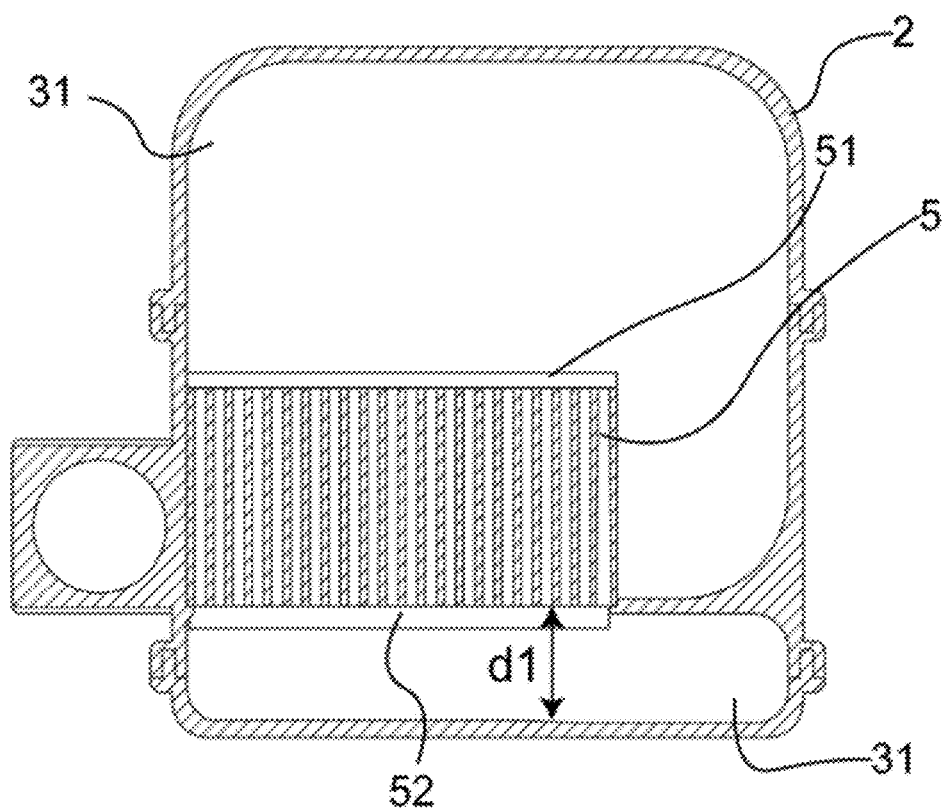
FIG. 13 is a schematic diagram of the distance between the ventilation component and the wall of the noise-reducing air passage device and its components in accordance with one embodiment.
Figure 14:
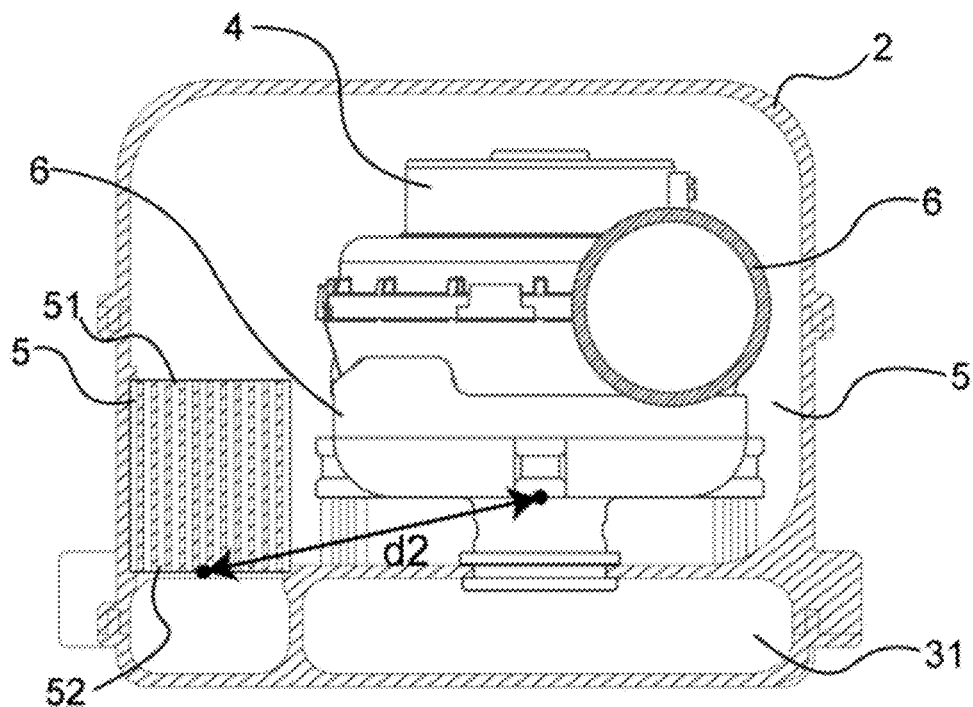
FIG. 14 is a schematic diagram of the straight-line distance between the exhaust end of the ventilation component and the blower inlet port of the noise-reducing air passage device and its components in accordance with one embodiment.

The noise-reducing air passage device 1 includes at least one ventilation component 5, provided within the gas passage 3 and configured to divide at least part of the gas. The ventilation component 5 is secured within the housing 2 and has multiple adjacent internal gaps to divide the gas flowing out of the chamber 31 into smaller gas flow units, which then pass through the internal gaps to the other side of the ventilation component 5. This arrangement helps to streamline turbulent airflow, reducing noise by at least 1.5 decibels (as shown in FIG. 12). In one configuration, the ventilation component 5 includes several parallel baffles, each separated by uniform internal gaps of the same width. These baffles are typically elongated and may have angled edges to facilitate better gas division. The baffles can also expand outwardly or contract inwardly, accelerating the gas as it passes through the internal gaps of the ventilation component 5. The ventilation component 5 can take various forms, including configurations where the baffles are arranged at different angles, either adjacent to or intersecting each other. To ensure smooth, noise-free passage of gas, the internal gaps of the ventilation component 5 range from 0.5 mm to 3.3 mm. In another variation, the ventilation component 5 has different outer wall shapes to fit the various internal spaces of the noise-reducing air passage device 1. For example, the ventilation component 5 can have square, hexagonal, or other shaped outer walls. When placed inside an inlet duct, the ventilation component 5 may have a circular wall that fits snugly against the duct's inner wall to facilitate noise reduction. Additionally, the ventilation component 5 may be a mesh structure with pores in the form of a weave, which may be made from any materials (including soft materials like thermoplastic elastomers, silicone, or hard materials like plastics). In some instances, the ventilation component 5 is made from one of the following materials: polypropylene, polycarbonate, polyethylene terephthalate-1,4-cyclohexane dimethanol ester, polyamide, or polyetheretherketone. When the noise-reducing air passage device 1 includes two chambers 31, the ventilation component 5 communicates with the first chamber and the second chamber, and parts of the ventilation component 5 are present in both chambers. To maintain the effectiveness of the ventilation component 5, there must be enough space for the gas to enter the ventilation component 5. Therefore, the distance between the exhaust end 52 of the ventilation component 5 and its opposing inner wall 23 of the housing should be greater than or equal to 5 mm (as shown in FIG. 13, d1≥5 mm). Preferably, this distance is at least 1.5 times the width of the ventilation component 5. Moreover, if the airflow path flowing through the gas passage 3 is too short, the gas passage 3 cannot effectively disperse the gas, resulting in poor noise reduction. Hence, the distance from the intake end 51 to the exhaust end 52 of the ventilation component 5 should be more than 10 mm. Additionally, the straight-line distance between the exhaust end 52 of the ventilation component 5 and the inlet port 41 of the blower 4 should be less than or equal to 15 mm (as shown in FIG. 14, d2≤15 mm).

The support component 6 within the gas passage 3 is configured as a perforated elastomer and at least part of the support component 6 has a non-uniform wall thickness to support the blower 4. At least one support component 6 is provided within the chamber 31 to support the blower 4 and to disperse vibrations during operation of the blower 4. At least one support component 6 is configured to at least partially contact the inner wall 23 of the housing. The non-uniform wall thickness of the support component 6 plays a crucial role in both damping vibrations and securing the blower 4. The support component 6 is provided with at least two thicknesses: the thicker sections provide stable support for the blower 4, firmly fixing the blower 4 within the chamber 31, while the thinner sections absorb the vibrations, thereby reducing noise effectively. In addition to the varying wall thickness, the support component 6 is configured as an elastomer with at least one hole. When the support component 6 includes more than one hole, these holes not only facilitate ventilation to prevent the blower 4 from overheating but also aid in vibration damping, similar to the effect of the thinner wall sections. For better support and fixing to the blower 4, the wall thickness of the support component 6 ranges from 0.6 mm to 3 mm, with a hardness of between Shore A20 to Shore A80. For sufficient support strength, the contact area between the support component 6 and the blower 4 is also critical, set to at least 330 mm². The support component 6 is made from materials such as silicone, rubber, thermoplastic elastomer, thermoplastic polyurethane, or fluoroelastomer.

Figure 15:
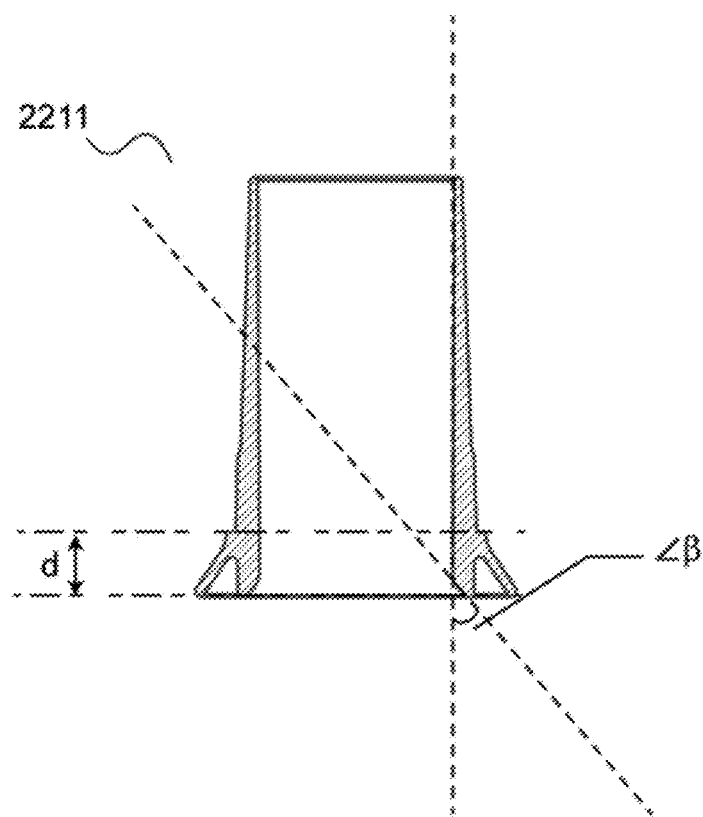
FIG. 15 is a schematic diagram of the taper of the inlet component of the noise-reducing air passage device and its components in accordance with one embodiment.

An inlet component 2211 is provided at the inlet 21, having at least one outwardly expanding wall to guide the gas gently into the chamber 31 (without turbulence or eddies). Specifically, the outwardly expanding elastomer smooths the airflow at the intake, reducing turbulence and speed differences, ensuring a more gentle and stable gas flow into the chamber 31. This gentle airflow effectively reduces collisions and vibrations within the chamber 31, thereby reducing noise. The inlet component 2211, made from an elastic material, can be directly or indirectly connected to the inlet 21 to ensure sealing and stability. The performance and efficiency of the inlet component 2211 are ensured by specific structural limits. The wall that extends outwardly of the inlet component 2211 (the outwardly expanding wall) forms an angle between 0.5° and 750 with the central axis of the inlet component 2211. Additionally, this angle can be understood as the angle formed between the outwardly expanding wall and the wall of the inlet component 2211. The length of the outwardly expanding wall of the inlet component 2211 ranges from 3 mm to 10 mm (as shown in FIG. 15, where ∠β is between 0.5° and 75°, and d ranges from 3 mm to 10 mm). This design ensures that the gas flows smoothly through the inlet component 2211 with little resistance. Additionally, the hardness of the inlet component 2211 ranges from Shore A20 to Shore A80, providing sufficient elasticity and stability. In this way, the inlet component 2211 enhances the efficiency and noise reduction effects of the noise-reducing air passage device 1, offering patients a more comfortable and quieter experience.

Figure 16:
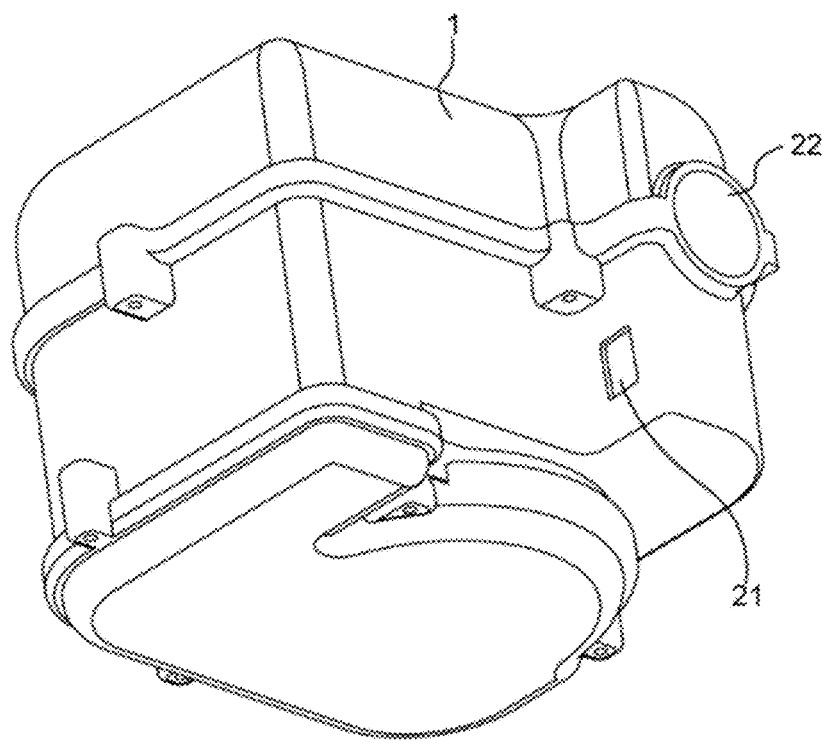
FIG. 16 is a schematic diagram of the inlet as a hole on the housing of the noise-reducing air passage device and its components in accordance with one embodiment.

In another embodiment, the inlet 21 can be one or more circular or non-circular holes on the housing, either connected to external components or directly drawing in air (as shown in FIG. 16).

Figure 17:
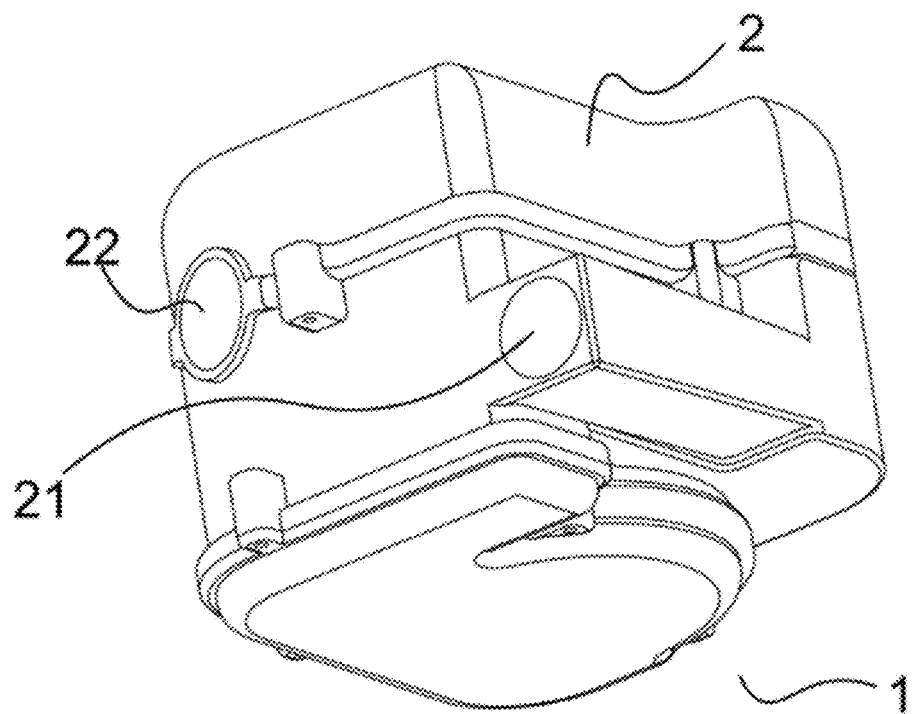
FIG. 17 is a schematic diagram of the inlet and outlet on the same wall of the housing of the noise-reducing air passage device and its components in accordance with one embodiment.

In another embodiment, the inlet 21 and outlet 22 are provided on the same side of the housing 2 (as shown in FIG. 17).

Figure 18:
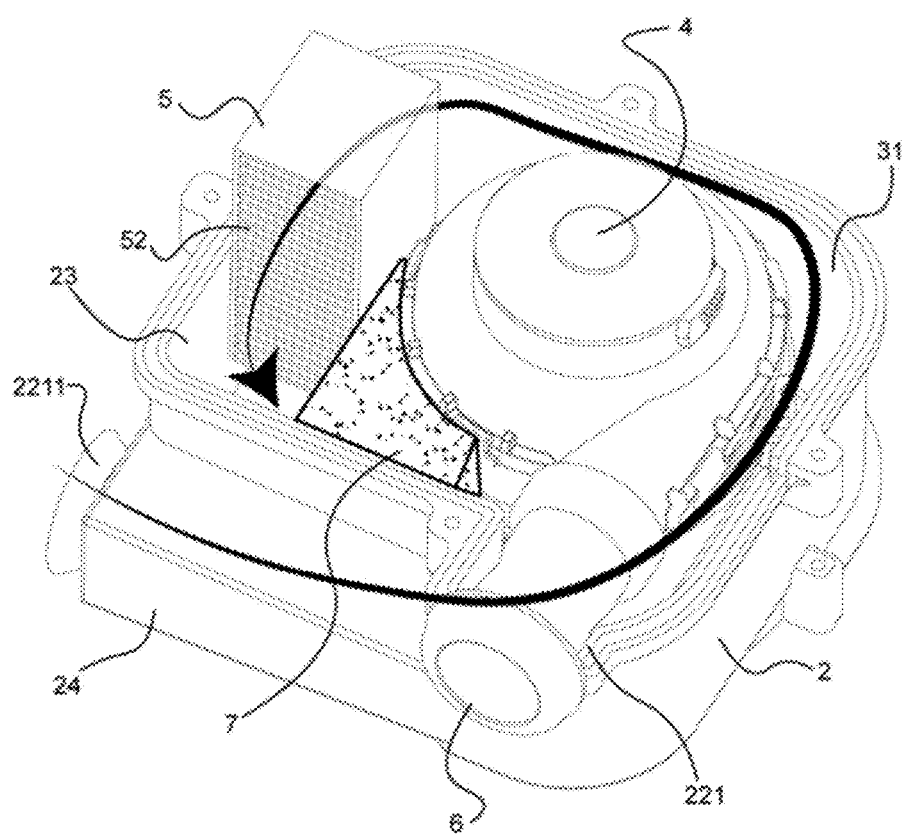
FIG. 18 is a schematic diagram of the ventilation component provided at another position within the gas passage of the noise-reducing air passage device and its components in accordance with one embodiment.

In another embodiment, the ventilation component 5 is provided at a different position within the gas passage 3 (as shown in FIG. 18).

Figure 19:
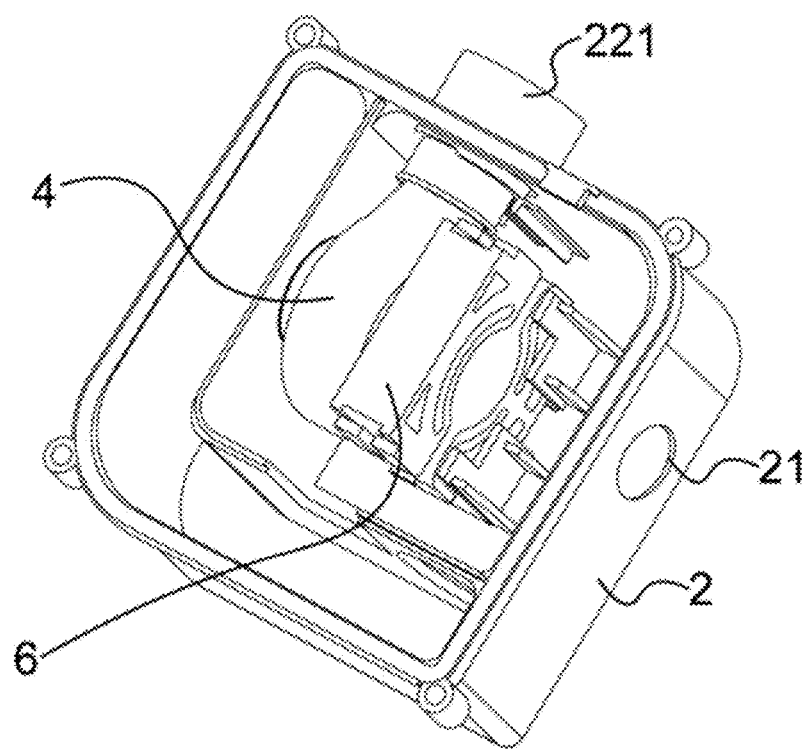
FIG. 19 is a schematic diagram of another form of the support component of the noise-reducing air passage device and its components in accordance with one embodiment.

In another embodiment, various forms of the support component 6 are used (as shown in FIG. 19).

Figure 20:
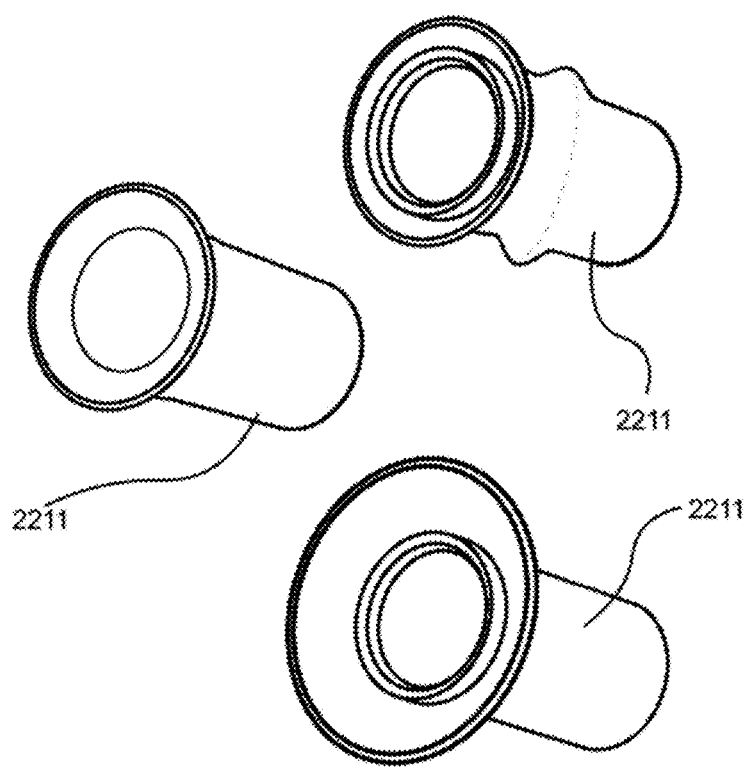
FIG. 20 is a schematic diagram of different forms of the inlet component of the noise-reducing air passage device and its components in accordance with one embodiment.

In another embodiment, the inlet component 2211 takes on different forms (as shown in FIG. 20).

In another embodiment, the inlet component 2211 is integrally formed with the housing.

Figure 21:
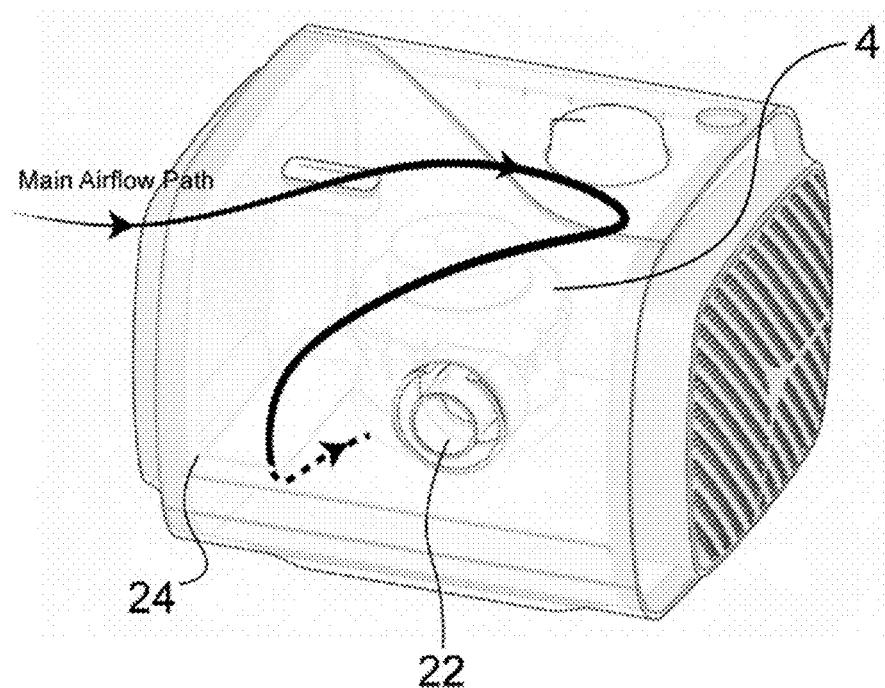
FIG. 21 is a three-dimensional schematic diagram of the housing of the noise-reducing air passage device and its components forming part of the positive pressure ventilation device in accordance with one embodiment.
Figure 22:
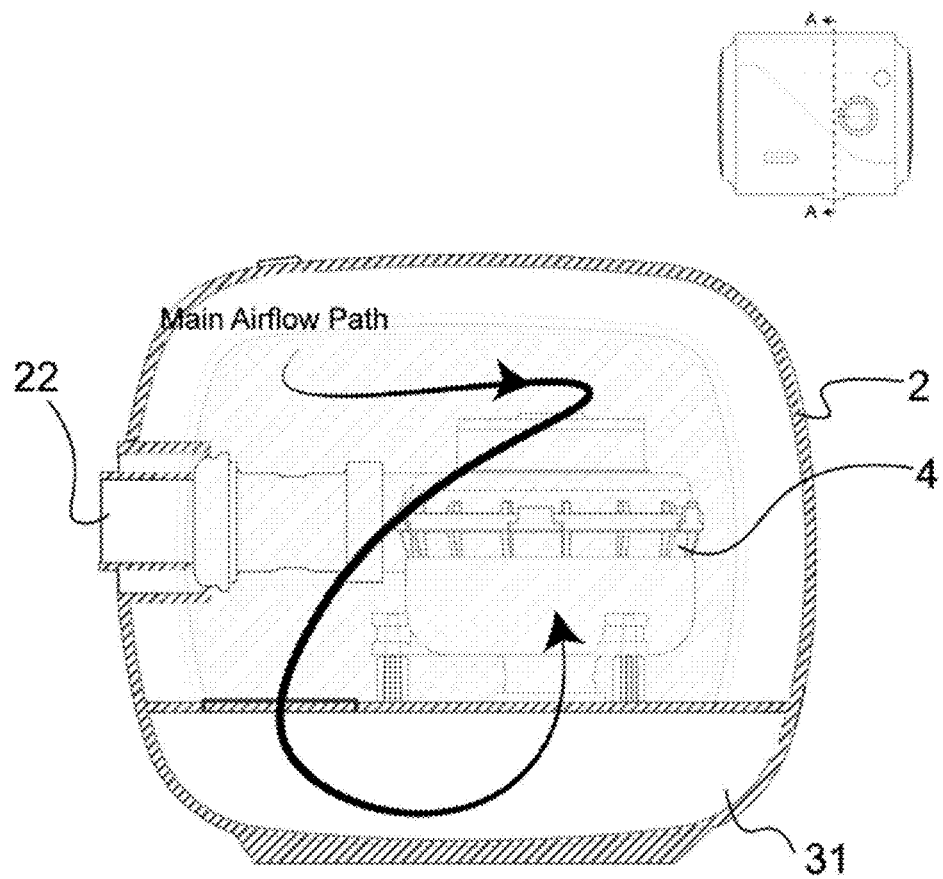
FIG. 22 is a cross-sectional view of the housing of the noise-reducing air passage device and its components forming part of the positive pressure ventilation device in accordance with one embodiment.

In another embodiment, the housing 2 of the noise-reducing air passage device 1 forms part of the positive airway pressure device (as shown in FIGS. 21 and 22). This means that the blower 4 is at least partially exposed inside the housing of the positive airway pressure device. In other words, the housing 2 of the noise-reducing air passage device 1 and the housing of the positive airway pressure device are at least partially the same, jointly forming the gas passage 3.

Embodiment 2

Figure 23:
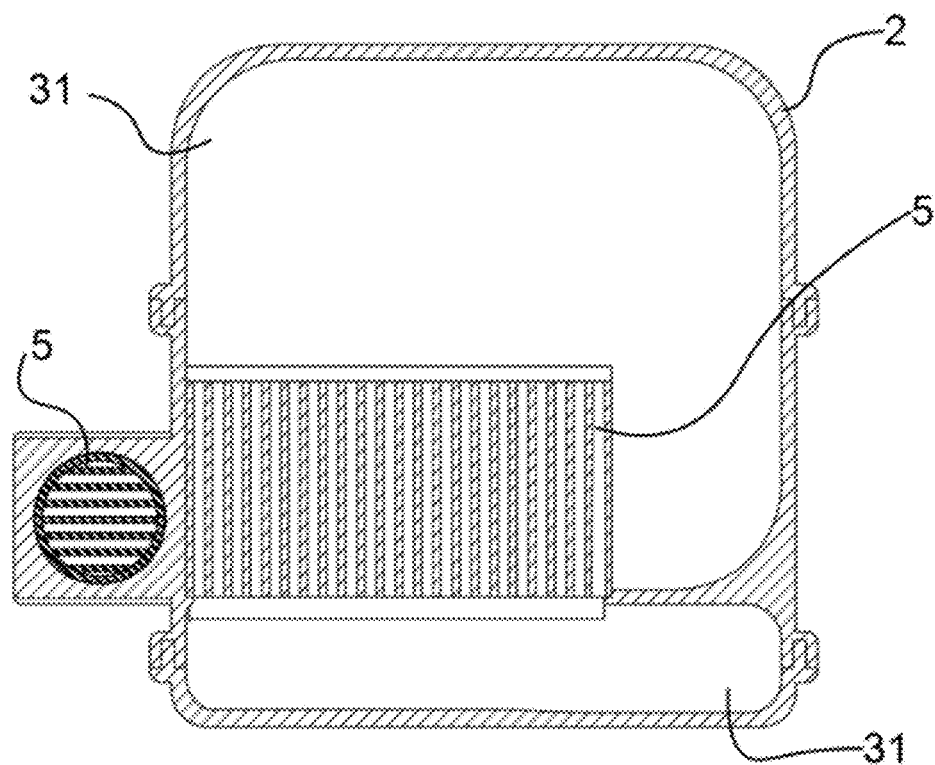
FIG. 23 is a cross-sectional view of the noise-reducing air passage device and its components with at least two different forms of ventilation components in accordance with one embodiment.
Figure 24:
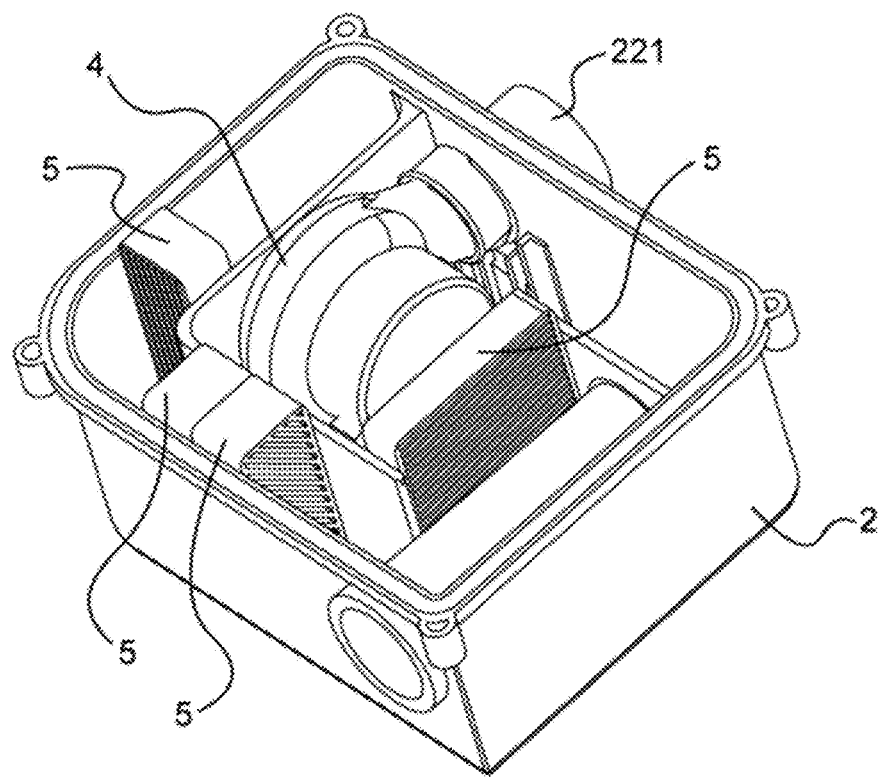
FIG. 24 is a schematic diagram of the noise-reducing air passage device and its components with at least two different forms of ventilation components in accordance with one embodiment.

This embodiment provides a noise-reducing air passage device 1 and its components for use in ventilator systems (refer to FIGS. 23 and 24). A sectional view and a three-dimensional schematic diagram of the noise-reducing air passage device 1 are provided. The noise-reducing air passage device 1 in this embodiment differs from that in Embodiment 1 by having at least two different forms of the ventilation component 5 within the gas passage 3. These different forms refer to variations in the internal baffle design of the ventilation component 5 (including baffle angles and taper, different internal gaps of the ventilation component 5, or different outer walls of the ventilation component 5 (e.g., square, round, or other shapes). The ventilation components 5 of the noise-reducing air passage device 1 can be individually placed in different chambers 31 to perform various functions or used in combination within one or more chambers 31. When multiple ventilation components 5 are provided within the gas passage 3, one implementation involves having several ventilation components 5 tightly fitted against each other, with their internal gaps interconnected. Specifically, the exhaust end 52 of one ventilation component 5 is tightly connected to the intake end 51 of another, creating a continuous gas flow passage. This design effectively lengthens the ventilation components 5, making the airflow path within the internal gaps longer and more intricate. As a result, the gas stays longer within the gas passage 3, further enhancing noise reduction. When ventilation components 5 with different baffle angles are used together, the airflow is initially divided into smaller streams upon entering the first form of ventilation component 5. Due to the different baffle angles in the second form of ventilation component 5, the airflow is further divided when it exits the first ventilation component 5 and enters the second ventilation component 5. This process further subdivides the already divided airflow into even smaller streams. Through this continuous division, the airflow speed gradually decreases, and the noise within the airflow is more effectively dispersed and reduced. The coordinated use of different forms of ventilation components 5 optimizes the airflow dynamics, making the gas flow within the gas passage 3 smoother and quieter. Additionally, the arrangement of the ventilation components 5 within the noise-reducing air passage device 1 can also involve spacing them apart. For instance, placing the first ventilation component 5 in the first chamber to slow down the airflow, while the second ventilation component 5 is placed between chambers to further modulate the airflow and to adjust the speed and direction of the airflow, helps in streamlining turbulent airflow throughout the gas passage 3, thus enhancing noise reduction over a larger area within the noise-reducing air passage device 1.

In another embodiment, multiple ventilation components 5 of the same form are used in a stacked configuration, either tightly fitted against each other or arranged with certain internal gaps between them.

Embodiment 3

Figure 25:
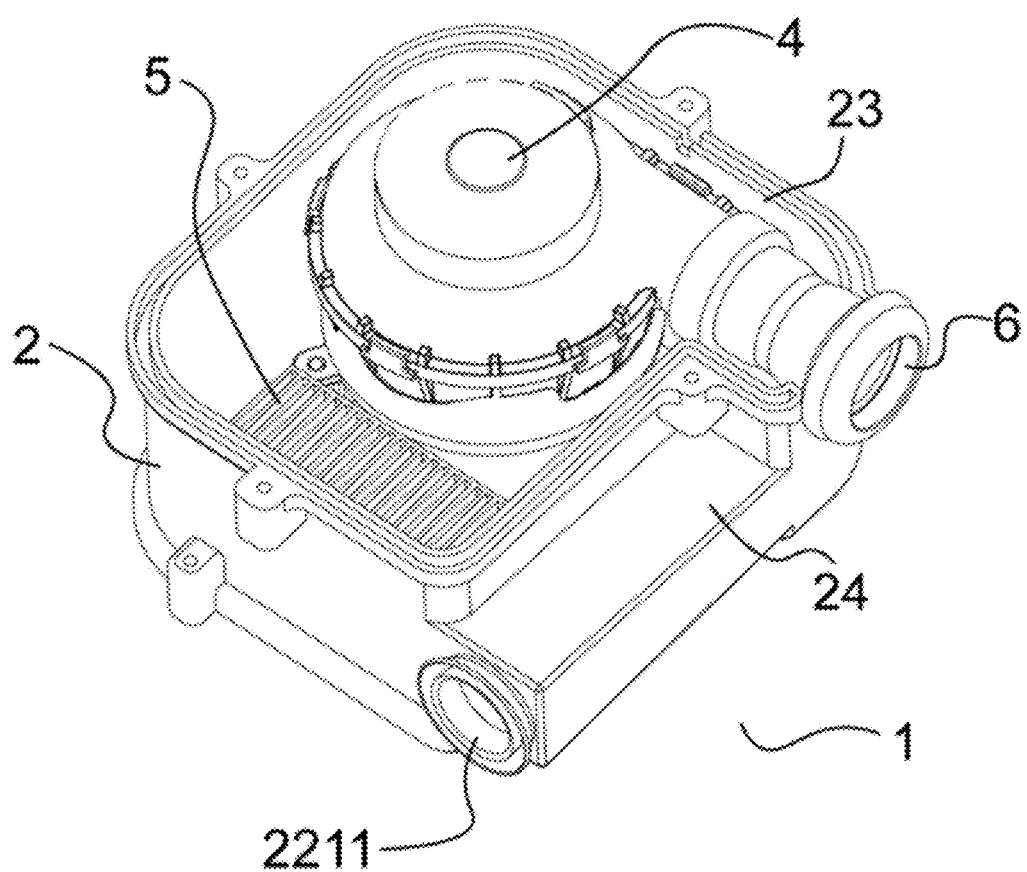
FIG. 25 is a schematic diagram of the noise-reducing air passage device and its components without using foam in accordance with one embodiment.

This embodiment provides a noise-reducing air passage device 1 and its components for use in ventilator systems (refer to FIG. 25). The three-dimensional schematic diagram of the noise-reducing air passage device 1 is provided to show the configuration of the device 1 without foam. This embodiment differs from embodiment 1 by reducing or eliminating the use of foam 7 within the noise-reducing air passage device 1. This disclosure achieves regulatory noise levels by utilizing various noise-reducing components and the internal spatial structure of the noise-reducing air passage device 1, thereby reducing or eliminating the need for foam 7. Consequently, this embodiment offers higher health and safety assurance for patients. This design reduces or eliminates the potential health risks associated with foam 7, such as the release of particles or respiratory irritation, further ensuring the safety and health of patients using the ventilator. Compared to traditional designs that rely on foam for noise reduction, the noise-reducing air passage device 1 with reduced foam 7 is not only safer but also easier to maintain due to its simpler internal structure, providing a more convenient and comfortable user experience for patients. Additionally, this embodiment simplifies the internal structure of the noise-reducing air passage device 1, thereby reducing production costs to some extent.

Embodiment 4

Figure 26:
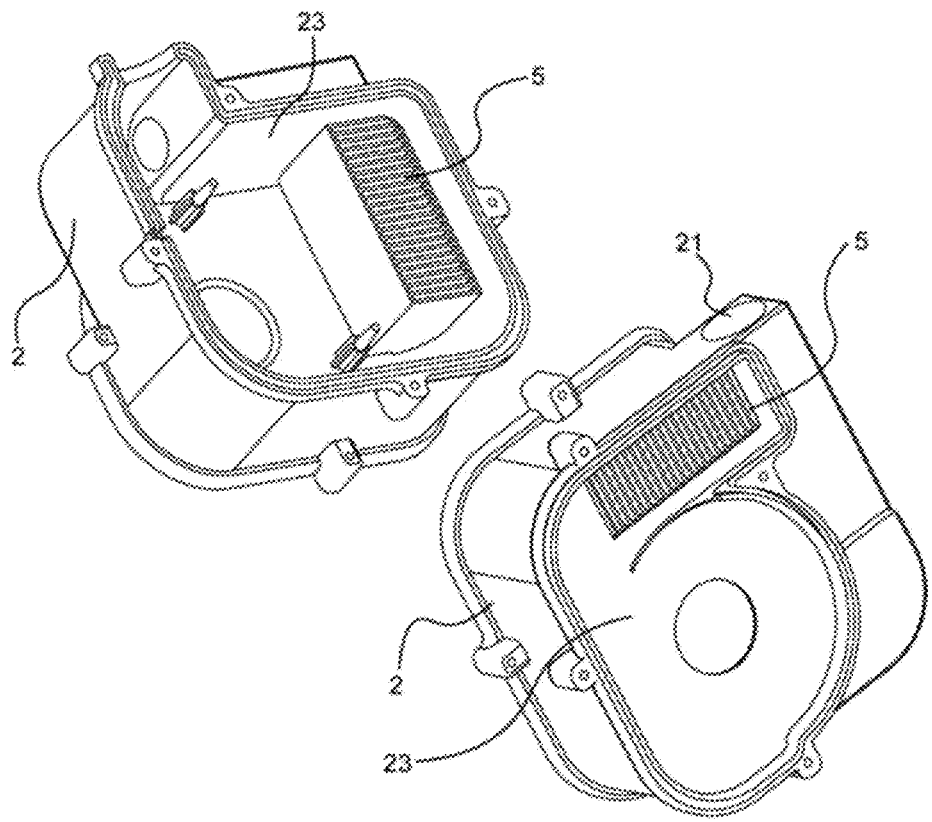
FIG. 26 is a schematic diagram of the ventilation component integrally formed with the housing in accordance with one embodiment.
Figure 27:
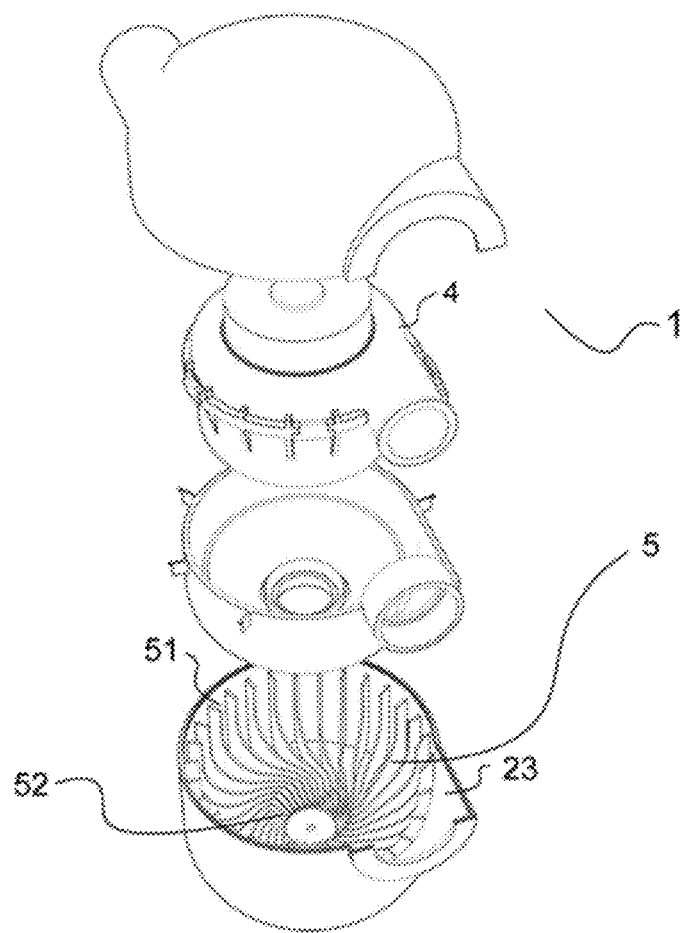
FIG. 27 is an exploded schematic diagram of another form of the ventilation component integrally formed with the housing in accordance with one embodiment.
Figure 28:
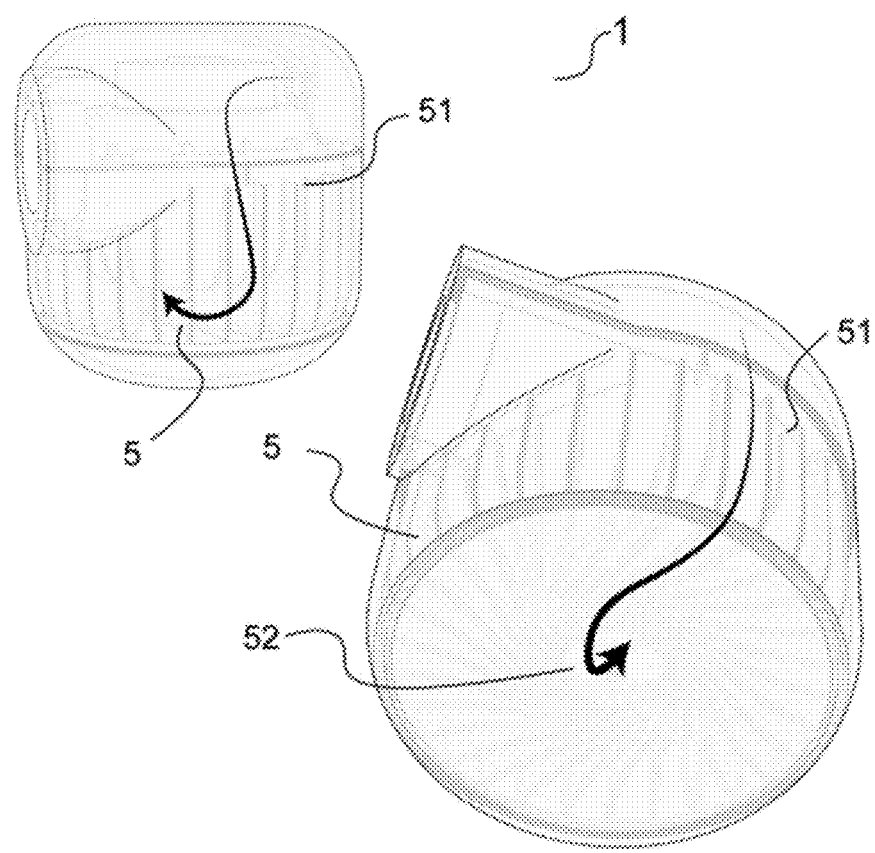
FIG. 28 is a schematic diagram of another form of the ventilation component integrally formed with the housing in accordance with one embodiment.

This embodiment provides a noise-reducing air passage device 1 and its components for use in ventilator systems (refer to FIGS. 26-28). The three-dimensional schematic diagrams are provided. This embodiment differs from Embodiment 1 in that the ventilation component 5 is integrally formed with the housing 2 (as shown in FIG. 21). In this embodiment, the structure of the ventilation component 5 is specifically configured as having an outer wall to merge with the wall of the housing 2. The outer wall is a part of the housing 2 of the noise-reducing air passage device 1, allowing for various designs. The outer wall of the ventilation component 5 can take multiple forms and may even be constituted by the chamber wall (as shown in FIGS. 27 and 28). The structure of the ventilation component 5 that reduces noise is a channel formed by baffles. When these baffles are shaped to have a specific form, they can guide or extend the gas flow path. For example, in this embodiment, the baffles shown in FIGS. 27 and 28 are arranged irregularly or in a specific pattern along the inner wall 23 of the housing 2 of the noise-reducing air passage device 1. Compared to baffles arranged along a straight line, this design more effectively guides airflow and extends the gas flow path within the noise-reducing air passage device 1. This design not only helps optimize the airflow but also adapts to the more complex structures of the inner wall 23 of the housing.

The implementation of a noise-reducing air passage device and its components at least includes the following benefits:

1. The disclosure utilizes various efficient noise-reducing components (such as inlet components, ventilation components, and support components) and structures within the noise-reducing air passage device. These include optimizing the volume ratio of the gas passage to the blower and designing the structure to extend the airflow path inside the air passage device. The combination of these noise-reducing components and structures, along with the layered arrangement of various noise-reducing components, effectively reduces noise by at least 15 decibels, thus meeting noise level requirements in FDA regulations. Most ventilators currently available on the market utilize foam as the primary noise-reducing material within their air passage devices. This not only poses potential health risks to patients, but also suffers from a decrease in noise reduction effectiveness over time due to foam degradation. In contrast to these traditional designs, which depend almost entirely on foam for noise reduction, this disclosure innovates by using the structure of the air passage device itself as the primary noise reduction method. This achieves regulatory noise levels with less or no foam usage. The noise-reducing structures and components in this disclosure use innovative designs and advanced materials to minimize noise transmission in the airflow, ensuring optimal silence during ventilator operation. Reducing noise through structure and components also decreases the potential for reduced airflow and volume, further enhancing the stability of ventilator performance. Overall, this efficient noise-reduction design not only improves patient comfort but also effectively reduces environmental noise, providing a quiet and comfortable sleep environment for the patient.

2. The design of efficient noise-reducing ventilation components offers advantages over traditional noise-reducing elements in terms of cost, installation, structure, and applicability. 1) This disclosure innovatively designs and uses ventilation components that achieve good noise reduction. Specifically, it smooths the originally chaotic airflow by channeling it through specific internal gaps within the structure. This process reduces noise by preventing the formation of turbulent flows or divergent air paths. As a single basic structural unit itself, this ventilation component has a straightforward design and is capable of reducing noise by at least 2 decibels, making it a notably efficient solution for noise reduction in its application. 2) The compact size of the ventilation component provided by this disclosure allows for a rational layout within the ventilator, occupying less space. Multiple ventilation components can be combined within the air passage device for enhanced noise reduction. Due to their simple structure, these ventilation components can be modified according to the space in the noise-reducing air passage device to become a standard structural formula, adaptable to different types of air passage devices, such as the ventilation component having a circular shape to match a circular channel in a noise-reducing air passage device. 3) Furthermore, the ventilation component is made from a single material and has a simple structure, simplifying the manufacturing process and making costs more controllable. The uniformity in structure and material allows manufacturers to scale production more easily and reduce costs through material optimization and process improvements. In contrast, existing ventilators in the market involve noise-reducing devices made from various materials with complex structures, making their manufacturing more cumbersome and costly. Therefore, the ventilation component provided by this disclosure offer a cost-effective advantage, providing patients with high-value products and promoting technical innovation and cost reduction in the ventilator industry.

3. The noise-reducing components used in the disclosure are detachable and can be used independently. While retaining the structure, their shape can be customized to fit various forms of noise-reducing air passage devices. Not only does the disclosure incorporate smooth and longer airflow paths to achieve noise reduction, but it also features several different types of detachable noise-reducing components that can be used independently. 1) These detachable noise-reducing components, such as inlet components, ventilation components, and support components, can be customized in shape and size to fit different forms and specifications of noise-reducing air passage devices. This provides a universal noise reduction solution for various models of ventilators, enhancing the product's applicability. In one approach, these detachable parts can be standardized to serve as universal components suitable for different noise-reducing air passage devices. In this way, manufacturers can produce large quantities of universal parts, thereby reducing production costs and enhancing production efficiency. 2) Since these noise-reducing components are used independently and are detachable, they can be replaced, maintained, and upgraded separately from the noise-reducing air passage devices. This reduces the ventilator's overall maintenance costs and future iteration costs. Furthermore, this form allows easy replacement or upgrading of noise-reducing components based on patient needs, meeting different requirements for noise reduction or personal preferences. This flexibility and customizability of the noise-reducing components provide a better experience for patients and bring more convenience in the use and maintenance of ventilators.

4. The noise-reducing components and structures provided by the disclosure can achieve regulatory noise levels within the air passage devices without using foam. Compared to existing ventilators on the market that almost always include foam in their noise-reducing air passage devices, this design enhances device safety, service life, and is environmentally friendly. The noise-reducing components and structures in this disclosure incorporate a series of innovative designs supported by theoretical and experimental data, resulting in a noise-reducing air passage device that lowers noise levels and still meets the regulatory requirements for noise levels without the use of foam. The benefits of reducing foam in the noise-reducing air passage devices can at least include: 1) Since placing foam within air passage devices is a common and effective method to meet regulatory noise levels, almost all respiratory machines on the market currently use foam materials in the air passage devices. However, tiny particles from decomposed foam materials can pose health risks when inhaled, particularly in respiratory machines used for prolonged periods and for long durations each time. Foam impacts human health in several significant ways: a. Chemical Exposure: Foam is typically made from synthetic materials such as polyurethane and polyether, which often include chemical additives or components. These chemicals can be released into the air during the ventilator's operation, becoming airborne contaminants. Prolonged inhalation of these substances can negatively affect both the respiratory system and overall health. b. Microbial Growth: Foam has moisture-absorbing properties, and in the humid environment created by ventilators, this can lead to the growth of bacteria and mold. Some ventilators also have humidification systems to increase patient comfort, which further enhances moisture absorption by the foam and promotes microbial growth. c. Particle Release: When the noise-reducing air passage device is in operation, the airflow causes the foam to vibrate and rub against other surfaces, leading to material degradation. This degradation can produce small particles. Additionally, the microbial growth in the foam due to its moisture retention can also lead to decomposition of the foam, releasing more particles. These particles are then inhaled by the patient, posing serious health risks. Furthermore, some patients may experience allergic reactions to foam, which can trigger respiratory allergies or asthma attacks, adversely affecting respiratory health. The noise-reducing air passage device in this disclosure achieves the regulatory noise levels with reduced use of foam or without foam, thereby reducing these health hazards. This not only ensures a safer respiratory environment for patients but also increases the competitiveness in the market, as it provides a health-conscious alternative to traditional designs. 2) Foam materials age and deteriorate quickly, making them the shortest-lived material within noise-reducing air passage devices compared to plastic materials. The presence of foam in existing designs reduces the lifespan of these air passage devices. This disclosure allows patients to opt for air passage devices with reduced foam, thereby extending the overall lifespan of the ventilator. Moreover, the absence of foam simplifies the internal structure of the noise-reducing air passage device. It eliminates the need for additional foam-fixing structures, reducing mechanical wear and maintenance needs, and enhancing the device's reliability and stability. 3) Foam, while a common noise-reduction material in ventilators, effectively reduces noise but has environmental impacts during its manufacture, use, and disposal. As a synthetic material, foam production consumes significant energy and resources and may involve the use of chemicals that contribute to pollution. Additionally, high-quality noise-reducing foam materials are usually costly, which, while reducing health risks, also increases the purchase cost of the device. The design of air passage devices with reduced foam reduces these issues. It not only lessens the negative environmental impact but also reduces waste production and saves costs on foam material purchases. 4) Reduced-foam air passage devices that still meet regulatory noise levels provide patients with more flexible options. Patients can choose whether to have foam within the noise-reducing air passage device or not. For those requiring quieter environments, such as patients with high demands for silence to improve sleep quality, they can opt for the noise-reducing device provided in this disclosure in combination with foam. Additionally, incorporating health-friendly materials like silicone or rubber within the noise-reducing air passage device can also reduce noise to some extent while eliminating the negative effects of foam.

The above description of the embodiments of the disclosure is provided with reference to the accompanying drawings. However, the disclosure is not limited to the specific embodiments described above. These specific embodiments are merely illustrative and not restrictive. Those skilled in the art, in light of the teachings of the disclosure, may make many modifications and variations without departing from the spirit and scope of the disclosure as defined by the claims. All such modifications and variations are within the protection scope of the disclosure.

It must be noted that as used herein and in the appended claims, the singular forms "a" "an", and "the" include their plural equivalents, unless the context clearly dictates otherwise.

The invention claimed is:

1. A noise-reducing air passage device and its components for use in ventilator systems, configured to provide pressurized gas to an airway of a patient, the noise-reducing air passage device and its components comprising:
   a housing, including at least one inlet, at least one outlet, an inner wall, and an outer wall, wherein a space enclosed by the inner wall of the housing forms a gas passage comprising at least one chamber to provide the space for gas accumulation and flow;
   a blower, secured within one of the at least one chamber, configured to allow flow of gas into the blower from an inlet port of the blower, pressurize the gas, and deliver the pressurized gas to the at least one outlet;
   an inlet component, comprising a wall, wherein the inlet component is configured to guide the gas without turbulence or eddies into the at least one chamber and at least one portion of the wall extends outwardly;
   at least one ventilation component, wherein the at least one ventilation component is provided within the gas passage and is configured to divide at least part of the gas; and
   at least one support component, configured as a perforated elastomer, wherein the at least one support component is provided within the at least one chamber to support the blower and to disperse vibrations during operation of the blower,
   wherein a longitudinal axis of the inlet port of the blower is transverse to a longitudinal axis of each of the at least one outlet in a top view plane, where the longitudinal axis of the inlet port is at least parallel to a direction in which the gas flows into the blower, and the longitudinal axis of the at least one outlet is at least parallel to a direction in which the pressurized gas flows out of the respective outlet.

2. The noise-reducing air passage device and its components according to claim 1, wherein the at least one ventilation component has an exhaust end to allow the gas to flow out, and a distance between the exhaust end and its opposing inner wall of the housing is at least 1.5 times a width of the at least one ventilation component.

3. The noise-reducing air passage device and its components according to claim 1, wherein the at least one portion of the wall that extends outwardly forms an angle between 0.5° to 75° with the wall of the inlet component.

4. The noise-reducing air passage device and its components according to claim 1, wherein a length of the at least one portion of the wall that extends outwardly of the inlet component is between 3 mm to 10 mm.

5. The noise-reducing air passage device and its components according to claim 1, wherein the at least one support component has at least two different thicknesses.

6. The noise-reducing air passage device and its components according to claim 1, wherein the housing of the noise-reducing air passage device forms part of a positive pressure ventilation device.

7. The noise-reducing air passage device and its components according to claim 1, wherein the housing of the noise-reducing air passage device comprises at least one material selected from the group consisting of polypropylene, polycarbonate, polyethylene terephthalate-1,4-cyclohexane dimethanol ester, polyamide, and polyetheretherketone.

8. A noise-reducing air passage device and its components for use in ventilator systems, configured to provide pressurized gas to an airway of a patient, the noise-reducing air passage device and its components comprising:
   a housing, including at least one inlet, at least one outlet, an inner wall, and an outer wall, wherein a space enclosed by the inner wall of the housing forms a gas passage comprising at least one chamber to provide the space for gas accumulation and flow;
   a blower, secured within one of the at least one chamber, configured to allow flow of gas into the blower from an inlet port of the blower, pressurize the gas, and deliver the pressurized gas to the at least one outlet; and
   at least one ventilation component, wherein the at least one ventilation component is provided within the gas passage and is configured to divide at least part of the gas, wherein a distance from an intake end to an exhaust end of the at least one ventilation component is greater than 10 mm, and wherein a distance from the exhaust end of the at least one ventilation component to its opposing inner wall of the housing is greater than or equal to 5 mm,
   wherein a longitudinal axis of the inlet port of the blower is transverse to a longitudinal axis of each of the at least one outlet in a top view plane, where the longitudinal axis of the inlet port is at least parallel to a direction in which the gas flows into the blower, and the longitudinal axis of the at least one outlet is at least parallel to a direction in which the pressurized gas flows out of the respective outlet.

9. The noise-reducing air passage device and its components according to claim 8, wherein the at least one ventilation component is secured within the housing and has internal gaps, and wherein the internal gaps are configured to divide the gas that flows out from the at least one chamber.

10. The noise-reducing air passage device and its components according to claim 9, wherein each of the internal gaps of the at least one ventilation component has a width between 0.5 mm to 3.3 mm.

11. The noise-reducing air passage device and its components according to claim 8, wherein an inlet component is provided at the at least one inlet, and a hardness of the inlet component is between Shore A20 to Shore A80.

12. The noise-reducing air passage device and its components according to claim 8, wherein a straight-line distance between the exhaust end of the at least one ventilation component and the inlet port of the blower is less than or equal to 15 mm.

13. The noise-reducing air passage device and its components according to claim 8, wherein the at least one ventilation component comprises at least one material selected from the group consisting of polypropylene, polycarbonate, polyethylene terephthalate-1,4-cyclohexane dimethanol ester, polyamide, and polyetheretherketone.

14. A noise-reducing air passage device and its components for use in ventilator systems, configured to provide pressurized gas to an airway of a patient, the noise-reducing air passage device and its components comprising:
a housing, including at least one inlet, at least one outlet, an inner wall, and an outer wall, wherein a space enclosed by the inner wall of the housing forms a gas passage comprising at least one chamber to provide the space for gas accumulation and flow;
a blower, secured within one of the at least one chamber, configured to allow flow of gas into the blower from an inlet port of the blower, pressurize the gas, and deliver the pressurized gas to the at least one outlet; and
at least one support component, configured as a perforated elastomer, wherein the at least one support component is provided within the at least one chamber to support the blower and to disperse vibrations during operation of the blower,
wherein the at least one support component has at least one of the following characteristics:
   a. at least part of the at least one support component in contact with the inner wall of the housing;
   b. at least part of a wall thickness of the at least one support component between 0.6 mm to 3 mm; and
   c. a hardness of the at least one support component between Shore A20 to Shore A80, and
wherein a longitudinal axis of the inlet port of the blower is transverse to a longitudinal axis of each of the at least one outlet in a top view plane, where the longitudinal axis of the inlet port is at least parallel to a direction in which the gas flows into the blower, and the longitudinal axis of the at least one outlet is at least parallel to a direction in which the pressurized gas flows out of the respective outlet.

15. The noise-reducing air passage device and its components according to claim 14, wherein the at least one chamber further comprises a first chamber and a second chamber, and the blower is provided within the first chamber.

16. The noise-reducing air passage device and its components according to claim 14, wherein at least part of the at least one support component has a non-uniform wall thickness.

17. The noise-reducing air passage device and its components according to claim 14, wherein a contact area between the at least one support component and the blower is at least 330 mm².

18. The noise-reducing air passage device and its components according to claim 14, wherein an outlet pipe is provided at the at least one outlet and is configured to be integrally formed with the housing.

19. The noise-reducing air passage device and its components according to claim 14, wherein the at least one support component includes at least one material selected from the group consisting of silicone, rubber, thermoplastic elastomer, thermoplastic polyurethane, and fluororubber.

20. A noise-reducing air passage device and its components for use in ventilator systems, configured to provide pressurized gas to an airway of a patient, the noise-reducing air passage device and its components comprising:
a housing, including at least one inlet, at least one outlet, an inner wall, and an outer wall, wherein a space enclosed by the inner wall of the housing forms a gas passage comprising at least one chamber to provide the space for gas accumulation and flow;
a blower, secured within one of the at least one chamber, configured to allow flow of gas into the blower from an inlet port of the blower, pressurize the gas and, deliver the pressurized gas to the at least one outlet;
at least one ventilation component, wherein the at least one ventilation component is provided within the gas passage and is configured to divide at least part of the gas, wherein a distance from an intake end to an exhaust end of the at least one ventilation component is greater than 10 mm, and wherein a distance from the exhaust end of the at least one ventilation component to its opposing inner wall of the housing is greater than or equal to 5 mm; and
at least one support component, configured as a perforated elastomer, wherein at least one support component is provided within the at least one chamber to support the blower and to disperse vibrations during operation of the blower, and wherein a thickness of at least part of the at least one support component wall is between 0.6 mm to 3 mm,
wherein a longitudinal axis of the inlet port of the blower is transverse to a longitudinal axis of each of the at least one outlet in a top view plane, where the longitudinal axis of the inlet port is at least parallel to a direction in which the gas flows into the blower, and the longitudinal axis of the at least one outlet is at least parallel to a direction in which the pressurized gas flows into the respective inlet.

21. The noise-reducing air passage device and its components according to claim 20, wherein the at least one chamber further comprises a first chamber and a second chamber.

22. The noise-reducing air passage device and its components according to claim 21, wherein the at least one ventilation component communicates with the first chamber and the second chamber, and parts of the at least one ventilation component are present in both chambers.

23. The noise-reducing air passage device and its components according to claim 22, wherein the at least one ventilation component is secured within the housing and has internal gaps, and wherein the internal gaps are configured to divide the gas that flows out from the first chamber.

24. The noise-reducing air passage device and its components according to claim 20, wherein multiple ventilation components, configured to fit against each other, are provided within the gas passage, and their internal gaps are interconnectable.

25. The noise-reducing air passage device and its components according to claim 20, wherein the at least one support component comprises at least one material selected from the group consisting of silicone, rubber, thermoplastic polyurethane, thermoplastic elastomer, and fluoroelastomer.

* * * * *